(12) United States Patent
Aguero VIllarreal et al.

(10) Patent No.: US 10,674,917 B2
(45) Date of Patent: Jun. 9, 2020

(54) DEVICE FOR THE MECHANICAL DETECTION OF UNDERLYING TISSUES

(71) Applicant: Board of Regents, The University of Texas System, Austin, TX (US)

(72) Inventors: Victor Efrain Aguero VIllarreal, San Antonio, TX (US); Daniela Sofia Arriaga Flores, San Antonio, TX (US); Jair Israel Castillo, San Antonio, TX (US); Ehab Abdelaziz, San Antonio, TX (US); Teja Guda, San Antonio, TX (US)

( * ) Notice: Subject to any disclaimer, the term of this patent is extended or adjusted under 35 U.S.C. 154(b) by 458 days.

(21) Appl. No.: 15/136,954

(22) Filed: Apr. 24, 2016

(65) Prior Publication Data

US 2016/0310006 A1    Oct. 27, 2016

Related U.S. Application Data

(60) Provisional application No. 62/152,470, filed on Apr. 24, 2015.

(51) Int. Cl.
*A61B 5/00*    (2006.01)

(52) U.S. Cl.
CPC .......... *A61B 5/0053* (2013.01); *A61B 5/4538* (2013.01); *A61B 5/4887* (2013.01); *A61B 5/442* (2013.01); *A61B 5/6885* (2013.01); *A61B 2562/0247* (2013.01)

(58) Field of Classification Search
CPC ............ A61B 5/0053; A61B 2090/064; A61B 2090/065; A61B 5/442; A61B 5/6885
See application file for complete search history.

(56) References Cited

U.S. PATENT DOCUMENTS

| | | | | |
|---|---|---|---|---|
| 3,933,148 A | * | 1/1976 | Wyler ................. | A61B 5/0053 600/557 |
| 4,159,640 A | * | 7/1979 | Leveque .............. | A61B 5/0053 73/81 |
| 4,269,193 A | * | 5/1981 | Eckerle .............. | A61B 5/02116 600/485 |
| 4,365,638 A | * | 12/1982 | Leveque .............. | A61B 5/0055 600/587 |
| 4,423,738 A | * | 1/1984 | Newgard ........... | A61B 5/02116 600/485 |
| 4,505,278 A | * | 3/1985 | Alban ................. | A61B 5/0053 600/398 |

(Continued)

FOREIGN PATENT DOCUMENTS

GB    2502074 A  *  5/2012

*Primary Examiner* — Sean P Dougherty
(74) *Attorney, Agent, or Firm* — Nevrivy Patent Law Group P.L.L.C.

(57) ABSTRACT

The invention provides a device for the mechanical detection of a specific underlying tissue in a subject, comprising a container, wherein the container comprises a probe, spring, sensor, and signal indicator, wherein when a mechanical force is applied to the probe, it is transmitted to the sensor, whereby the sensor provides the signal indicator with a signal and the signal indicator indicates to the user an indication of detection of the specific underlying tissue in the subject. The sensor of the invention can be an electrical sensor such as a piezoelectric force transducer or a balloon. The invention also provides a method of performing a cricothyrotomy using the device.

22 Claims, 19 Drawing Sheets

(56) References Cited

U.S. PATENT DOCUMENTS

| | | | | |
|---|---|---|---|---|
| 5,115,808 A * | 5/1992 | Popovic | A61B 5/0051 | 600/438 |
| 5,224,469 A * | 7/1993 | Mocny | A61H 39/04 | 600/587 |
| 5,785,663 A * | 7/1998 | Sarvazyan | A61B 1/0052 | 600/561 |
| 5,833,633 A * | 11/1998 | Sarvazyan | A61B 1/0052 | 600/587 |
| 5,833,634 A * | 11/1998 | Laird | A61B 5/0053 | 600/587 |
| 5,836,894 A * | 11/1998 | Sarvazyan | A61B 1/0052 | 600/587 |
| 5,879,312 A * | 3/1999 | Imoto | A61B 5/0053 | 600/587 |
| 5,904,658 A * | 5/1999 | Niederauer | A61B 5/0053 | 600/587 |
| 5,922,018 A * | 7/1999 | Sarvazyan | A61B 1/0052 | 600/587 |
| 6,063,044 A * | 5/2000 | Leonard | A61B 5/0053 | 600/587 |
| 6,168,572 B1 * | 1/2001 | Vexler | A61B 5/0051 | 600/587 |
| 6,186,962 B1 * | 2/2001 | Lloyd | A61B 5/0053 | 128/903 |
| 6,351,549 B1 * | 2/2002 | Souluer | A61B 5/0053 | 382/131 |
| 6,511,427 B1 * | 1/2003 | Sliwa, Jr. | A61B 5/4869 | 600/438 |
| 6,659,967 B1 * | 12/2003 | Steinberg | A61B 5/0053 | 600/561 |
| 7,648,470 B2 * | 1/2010 | Omata | A61B 5/103 | 600/587 |
| 7,966,866 B2 * | 6/2011 | Hansma | A61B 5/0053 | 73/81 |
| 8,246,553 B2 * | 8/2012 | Sakagami | A61B 5/0053 | 600/553 |
| 8,328,730 B2 * | 12/2012 | Sakagami | A61B 5/0053 | 600/553 |
| 8,357,152 B2 * | 1/2013 | Govari | A61B 5/06 | 606/41 |
| 8,758,271 B2 * | 6/2014 | Hunter | A01G 7/00 | 600/587 |
| 9,265,461 B2 * | 2/2016 | Hunter | A61B 5/0053 | |
| 9,326,700 B2 * | 5/2016 | Govari | A61B 5/06 | |
| 9,888,883 B2 * | 2/2018 | Ellingsen | A61B 5/0051 | |
| 2008/0051704 A1 * | 2/2008 | Patel | A61L 29/04 | 604/95.05 |
| 2010/0087756 A1 * | 4/2010 | Egorov | A61B 5/0053 | 600/587 |
| 2011/0054357 A1 * | 3/2011 | Egorov | A61B 5/4337 | 600/591 |
| 2013/0085413 A1 * | 4/2013 | Tsamir | A61B 5/0053 | 600/567 |
| 2013/0090573 A1 * | 4/2013 | Shaker | A61B 5/4211 | 600/593 |
| 2013/0102930 A1 * | 4/2013 | Connor | A61B 1/267 | 600/590 |
| 2014/0142438 A1 * | 5/2014 | Ludwin | A61B 5/0053 | 600/481 |
| 2014/0187916 A1 * | 7/2014 | Clark | A61B 5/6885 | 600/424 |
| 2016/0157816 A1 * | 6/2016 | Denny | A61B 8/0858 | 600/449 |

* cited by examiner

Neck midlines diagram with ideal accuracy limits.

FIG. 10
A.
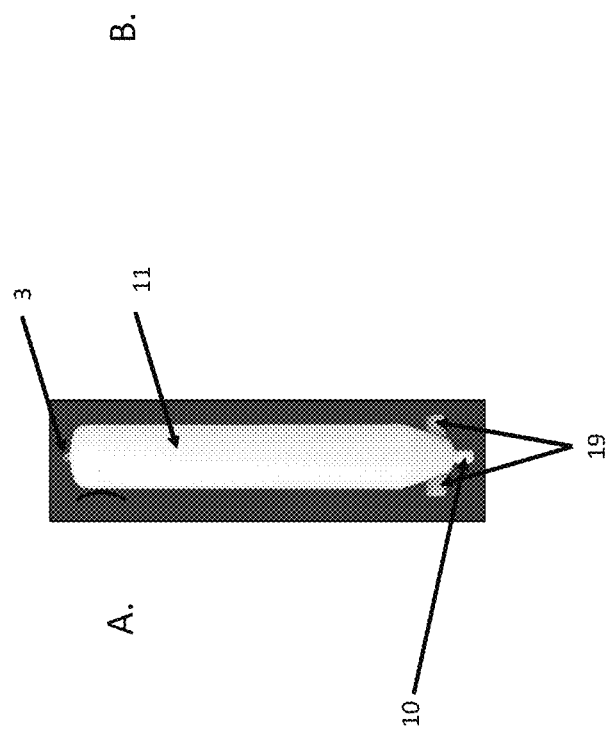
B.

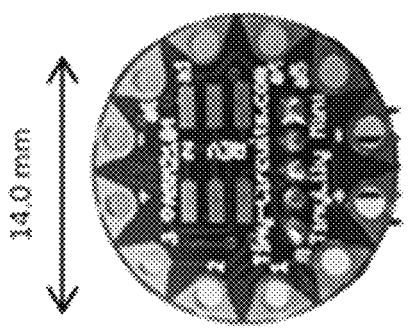
FIG. 11

A. Peak von Mises stress under an applied concussive pressure of 40 kPa

B. URES static displacement plot under applied pressure of 40 kPa.

A. Peak von Mises stress under an applied primary shockwave of 70 kPa

B. URES static displacement plot under applied pressure of 70 kPa

B. URES static displacement plot under applied force of 2.0 N

A. Peak von Mises stress under applied force of 2.0 N

DEVICE FOR THE MECHANICAL DETECTION OF UNDERLYING TISSUES

CROSS-REFERENCE TO RELATED APPLICATIONS

This application claims the benefit of U.S. Provisional Application No. 62/152,470, filed Apr. 24, 2015, the contents of which are hereby incorporated by reference in their entirety.

FIELD OF THE INVENTION

The present invention generally relates at least to the fields of medicine and medical devices.

BACKGROUND OF THE INVENTION

Cricothyrotomy (also called Cricothyroidotomy) is a lifesaving procedure to create an alternative airway in emergency situations. The cricothyroid membrane is a useful place to access the airway in the case of glottis and subglottic obstruction, injury, facial muscles spams or laryngospasm, uncontrollable emesis, upper airway stenosis or congenital deformities, clenched teeth, tumor, cancer and nose bleeding. Locating the cricothyroid membrane (CTM) during a cricothyrotomy procedure can prove challenging especially in the case of obese patients, women and children due to the difficulty in isolating anatomical landmarks. Currently, this procedure is contraindicated for children younger than 12 years old due to their smaller cricothyroid membrane and a more funnel-shaped, rostral and compliant larynx.

Cricothyrotomy is restricted to experienced or high level EMT's, paramedics, anesthesiologists and emergency physicians. Cricothyrotomy is an emergency procedure, which usually lasts <1 minute. Detection itself can last from 15 to up to 30 seconds.

The cricothyroid membrane (CTM) is small and surrounded by adjacent structures—including the cricothyroid muscles, thyroid and cricoid cartilages, and central cricothyroid arteries. Damage to any of these surrounding structures accounts for up to 40% failure in practice and can lead to perichondritis, stenosis, subcutaneous emphysema, hemorrhage, pneumothorax, laceration of esophagus or trachea, and anoxia. Delayed complications include tracheomalacia, bleeding, infection, fistulae, displacement and scarring.

There are currently two approaches to detect the cricothyroid membrane. The first one is palpation, which is done by emergency medical technicians (EMTs), army medics and other first response services. Palpation is highly inaccurate and biased but is the most common used in the medical field. The second approach is ultrasound, which is done in the hospitals under controlled conditions. Ultrasound is expensive, slow to operate, relatively bulky, requires a specific probe for soft tissue and is rarely available in the field. The approximate cost of a 2D, Doppler and M mode ultrasound from Sonosite, such as MicroMaxx is >$1500.

The time factor is an aspect to be considered for detecting CTM, since this emergency health care procedure operates in the "golden hour". If a device cannot detect CTM in a reasonable amount of time, there would be no practical use for it in the field. More importantly, in a patient that has been without oxygen for more than 5 minutes, it is unlikely that the patient will survive, and even if they do, there is a high possibility of brain damage. Thus, a device must be able to identify the cricothyroid membrane within a matter of seconds.

There is also a need for a device to detect other types of tissues. For example, X-ray is a traditional form to detect bone fractures. However, cartilage and tendons are difficult to visualize by X-rays in children.

Accordingly, there is a need for a rapid detection system to help health care providers detect underlying tissues in an accurate way, for example, in a cricothyrotomy procedure.

SUMMARY OF THE INVENTION

It is to be understood that both the foregoing general description of the embodiments and the following detailed description are exemplary, and thus do not restrict the scope of the embodiments.

In one aspect, the invention provides a device capable of detecting the differences in the stiffness of underlying tissues, which predicts the location of one or more tissues in a subject. In some embodiments, the one or more tissues are selected from cartilage, tendon, bone, muscle, blood vessels, and cricothyroid membrane.

In another aspect, the invention provides a device that provides a fast, accurate, portable, cost-effective and user-friendly detection system for the cricothyroid membrane.

In some embodiments, the invention provides a device that is simple, accurate, cost-effective, unbiased, improves the confidence of paramedics, is portable, doesn't need additional parts, and can incise and detect the cricothyroid membrane within seconds. In some embodiments, the device is able to detect cartilage and tendon without the need to expose the patient to radiation and go through the standard procedure for x-ray imaging. In some embodiments, the invention does not entirely depend upon anatomical landmarks.

In some embodiments, the device comprises a container, wherein the container holds a probe, spring, sensor, and signal indicator, wherein when a mechanical force is applied to the probe, it is transmitted to the spring and sensor, whereby the sensor provides a signal to the signal indicator. In some embodiments, the sensor is a piezoelectric force transducer. In some embodiments, the sensor is a balloon.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

FIG. 10. An embodiment of the invention. Panel A is an example of the invention with LED signal indicator (3), Probe (10), and Container (11) with two horizontal members at an end (19). Panel B is an embodiment of the invention being used to locate the CTM.

FIG. 11. Piezoelectric force transducer sensor (diameter 14 mm) compared in size to a dime.

DETAILED DESCRIPTION

Figure 1:
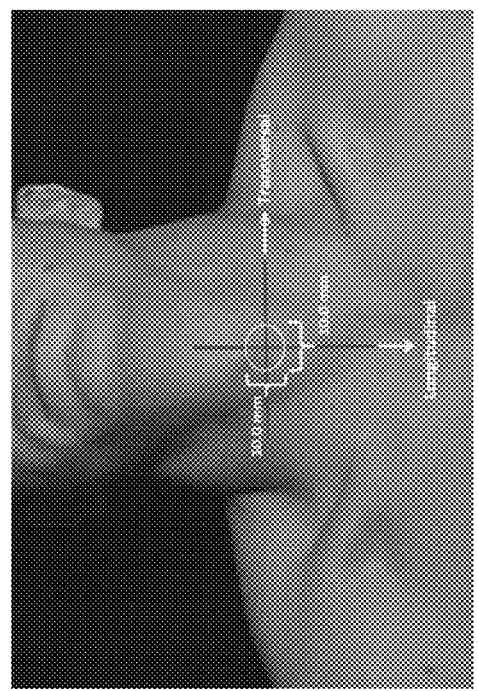
FIG. 1. Neck midlines diagram with ideal accuracy limits.

Reference will now be made in detail to embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the term "about" means at most plus or minus 10% of the numerical value of the number with which it is being used.

In one aspect, the invention provides a device capable of detecting the differences in the stiffness of underlying tissues, which predicts the location of one or more anatomical features in a subject. In some embodiments, the one or more anatomical features is selected from cartilage, tendon, bone, muscle, blood vessels, and a cricothyroid membrane.

In some embodiments, the invention provides a fast, accurate, portable, cost-effective and user-friendly detection system for cricothyroid membrane. In some embodiments, the invention has an accuracy of 80% or greater with an average detection time of 15 seconds. In some embodiments, the invention is rugged and capable of being stored and used in extreme environments. In some embodiments, the invention is able to withstand harsh temperatures and blast pressures of −4 to 140° F. and 70 kPa, respectively. These features make the invention suitable for operation under combat and civilian settings.

In some embodiments, the invention provides a device for the mechanical detection of a specific underlying tissue in a subject, comprising a container, wherein the container comprises a probe, spring, sensor, and signal indicator, wherein when a mechanical force is applied to the probe, it is transmitted to the spring and sensor, whereby the sensor provides a signal to the signal indicator which then provides an indication of detection.

The shape of the container is not particularly limiting. In some embodiments, the container is in the shape of a cylinder. In some embodiments, one end of the cylinder has the shape of a cone. In some embodiments, the container is ergonomically shaped to fit the hand of a user. In some embodiments, one end of the container comprises one or more horizontal members perpendicular to the major axis of the container. In some embodiments, the one or more horizontal members can be folded to be parallel with a major axis of the container. In some embodiments, the container is in the shape of a cylinder with a flange or one or more horizontal members perpendicular to the axis of the cylinder and at an end of the cylinder. In some embodiments, the container is in the shape of a cylinder with an end of the cylinder having the shape of a cone with two horizontal members perpendicular to the axis of the cylinder near the tip of the cone.

In some embodiments, an end of the container comprises a different material than the remainder of the container. In some embodiments, the end of the container having the probe comprises an elastic material. In some embodiments, the elastic material is a rubber or silicon material. In some embodiments, the end of the container having the probe is a rubber material in the shape of a cone or half sphere. In some embodiments, the end of the container having the probe comprises an elastic material and a hard material at the very tip. The hard material can be a material with low or no friction to facilitate sliding of the material across the skin of a patient.

The materials that can be used for the making of the container are not limiting, and can include, e.g., one or more plastics or metals. In some embodiments, the container is made of Ultra High Molecular Weight (UHMW) polyethylene.

The materials that can be used for the making of the probe are not limiting, and can include, e.g., one or more plastics or metals. In some embodiments, the probe is metal. In some embodiments, the probe is plastic. In some embodiments, the probe is UHMW polyethylene.

In some embodiments, the container has attached thereto a member for cutting tissue. In some embodiments, the member is retractable. In some embodiments, the member is a retractable scalpel. The member for cutting tissue can be located at an end opposite the container end with the probe tip or at the same end as the probe tip.

In some embodiments, the probe is a substantially elongated member with a first end configured to contact with the spring or a spring pin and a second end having a narrower surface area for contacting with a discrete region of the surface of the patient's body. In some embodiments, the first end is configured to be held by the spring and compress the spring when force is applied to the probe. In some embodiments, the first end is configured to push against a surface of a spring pen. In some embodiments, the second end is a point or blunt end. Any suitable shape may be used for the second end of the probe and is not limiting. The second end of the probe should not injury the patient when firmly pressed against the skin. In some embodiments, the second end of the probe does not protrude from an end of the container. In some embodiments, the second end of the probe contacts with an end of the container. In some embodiments, the end of the container contacting the second end of the probe can be comprised of an elastic material so that force applied to the end of the container when it is pressed against tissue is transmitted to the probe tip. In some embodiments, the second end of the probe is immobilized in elastic material at the end of the container but does protrude or partially protrudes from the end of the container.

In some embodiments, the second end of the probe or probe tip is responsible for the accuracy of the device to some extent. Usually, the finer the dimensions of the tip the more accurate the device would be. Nevertheless, in some embodiments, the device is designed to only differentiate the mechanical properties of the hyaline cartilage and the membrane ligament. Therefore, if the probe touches the membrane at the boundary of the cartilage it would still mark it as a place to incise. Hence, in some embodiments, the second end of the probe or probe tip is very blunted to detect the cricothyroid membrane as far as possible from the boundaries of cartilage tissues. The shape of the probe tip is not limited. In some embodiments, the probe tip has a wheel or roller to enhance sliding of the probe tip across the surface of a patient's neck.

In some embodiments, the first end of the probe contacts a spring within the container and a second end of the probe protrudes outside of the container. In some embodiments, the container further comprises a spring pin at an end of the spring that contacts with the probe. The materials that can be used for the making of the spring pin are not limiting, and can include, e.g., one or more plastics or metals. In some embodiments, the spring pin is plastic. In some embodiments, the spring pin is UHMW polyethylene.

The length of the device is not particularly limiting, and preferably the device is portable. In some embodiments, the device is from 100-250 mm in length. In some embodiments, the device is about 132 mm in length, about 147 mm in length, about 191 mm in length, or about 221 mm in length. In some embodiments, the device can be about 100 mm, 110 mm, 120 mm, 130 mm, 140 mm, 150 mm, 160 mm, 170 mm, 180 mm, 190 mm, 200 mm, 210 mm, 220 mm, 230 mm, 240 mm, or 250 mm in length.

The spring that can be used is not limiting. The spring should not be too stiff as to not be compressible against the skin of a patient without causing injury. In some embodiments, the spring is made of metal, metal alloy, or plastic. In some embodiments, the spring is made of steel. In some embodiments, the spring is a compression coil spring. In some embodiments, the spring has a spring constant of between about $k=100$ N/m and 2000 N/m. In some embodiments, the spring has a spring constant of between about $k=200$ N/m and 1300 N/m. In some embodiments, the spring has a spring constant of between about $k=290$ N/m and 800 N/m. In some embodiments, the spring has a spring constant of between about $k=290$ N/m and 500 N/m. In some embodiments, the spring has a spring constant of about $k=500$ N/m, $k=490$ N/m, $k=480$ N/m, $k=470$ N/m, $k=460$ N/m, $k=450$ N/m, $k=440$ N/m, $k=430$ N/m, $k=420$ N/m, $k=410$ N/m, $k=400$ N/m, $k=390$ N/m, $k=380$ N/m, $k=370$ N/m, $k=360$ N/m, $k=350$ N/m, $k=340$ N/m, $k=330$ N/m, $k=320$/m, $k=310$ N/m, $k=300$ N/m, $k=290$ N/m, $k=280$ N/m, k=270 N/m, k=260 N/m, k=250 N/m, k=240 N/m, k=230 N/m, k=220 N/m, k=210 N/m, k=200 N/m, k=190 N/m, k=180 N/m, k=170 N/m, k=160 N/m, k=150 N/m, k=140 N/m, k=130 N/m, k=120 N/m, k=110 N/m, or k=100 N/m. In some embodiments, the spring has a spring constant of about k=293.06 N/m. In some embodiments, the spring has a spring constant of about k=333.06 N/m. In some embodiments, the spring has a spring constant of about k=1180.33 N/m. In some embodiments, the spring consists of 8-14 coils, with a diameter of about 0.014 m and a wire thickness of about 0.001 m.

In some embodiments, an end of the spring contacts the sensor and directly transfers a force applied to the probe to the sensor. In some embodiments, an end of the spring contacts one or more intermediate members and indirectly transfers a force applied to the probe to the sensor. In some embodiments, the spring contacts the container and force is transferred to the sensor by the probe or spring pin.

In some embodiments, the device comprises a cushion. The cushion can be made of any suitable material and is not limited. In some embodiments, the cushion is made of UHMW polyethylene, PLA plastic or ABS plastic. In some embodiments, the cushion is made of a material with a lower elastic modulus than the material of the container. In some embodiments, the container comprises UHMWPE and the cushion comprises PLA or ABS plastic. In some embodiments, the cushion is located between the sensor and an end of the container not having the probe. In some embodiments, the cushion provides a solid surface contacted with the sensor and absorbs the impact of the probe or probe pin without damaging the device. In some embodiments, damage to the device can be avoided by having the cushion have a lower elastic modulus than the material of the container. In some embodiments, the cushion is configured to fill the space between the end of the container and the sensor. In some embodiments, the cushion protects electronic circuitry such as resistors or IC circuit from damage by use of the device.

Any suitable sensor capable of detecting the mechanical force of the probe or a change in mechanical force of the probe can be used. In some embodiments, the sensor is a mechanical or electrical sensor. In some embodiments, the sensor is a piezoelectric force transducer. In some embodiments, the sensor is a balloon. In some embodiments, the sensor is encased in a water-proof container.

In some embodiments, the diameter of the entire piezoelectric force transducer is selected from about 10 mm, about 15 mm, about 20 mm, about 25 mm and about 30 mm.

In some embodiments, the diameter of the sensing part of the entire piezoelectric force transducer is selected from about 5 mm, about 10 mm, about 15 mm, and about 20 mm.

In some embodiments, the sensor is a balloon that is a force transducer. The balloon can be filled with gas or liquid and is not limiting. In some embodiments, the balloon is filled with air. In some embodiments, the filled balloon has a volume of about $1\times10^{-6}$ m$^3$ to $5\times10^{-6}$ m$^3$. In some embodiments, the filled balloon has a volume of about $9.17\times10^{-7}$ m$^3$. In some embodiments, the gauge pressure in the balloon is between about 35000 Pa and about 60,000 Pa. In some embodiments, the gauge pressure in the balloon is about 60 kPa or about 160 kPa absolute pressure. In some embodiments the absolute pressure is 160,069 kPa. The balloon can be made of any suitable material and is not limited. In some embodiments, the balloon is made of polyethylene non-porous film.

In some embodiments, the diameter of the container is sufficient to hold the sensor in place.

Any suitable signal indicator can be used that provides an indication to a user. In some embodiments, the signal indicator provides a sound indication, a vibration indication or a light indication, or a combination thereof. In some embodiments, the signal indicator is a light source that provides a light indication. In some embodiments, light source is a light emitting diode (LED). In some embodiments, the LED is about 2 Volts. In some embodiments, the invention has a second indication. In some embodiments, this second indication is a backup in case the first indication fails. In some embodiments, the first indication is a light and the second indication is a sound.

In some embodiments, the signal indicator is a gage with an analog or digital display. In some embodiments, the gage is a pressure gage. In some embodiments, the pressure gage provides a different signal or readout for different balloon pressures. In some embodiments, the pressure gage will detect a gauge pressure difference of 27 kPa. In some embodiments, the pressure gage has a range of 0 to 100 kPa. The sensitivity of the pressure gage is not limiting. Any suitable pressure gage capable of detecting a pressure correlating with a desired tissue may be used.

In some embodiments, the device is calibrated to detect a specific tissue selected from the group consisting of cartilage, tendon, bone, muscle, blood vessels, and the cricothyroid membrane. In some embodiments, the specific underlying tissue is thyroid and cricoid cartilage.

In some embodiments, the sensor measures a force of about 1.0 N, about 1.1 N, about 1.2 N, about 1.3 N, about 1.4 N, about 1.5 N, about 1.6 N, about 1.7 N, about 1.8 N, about 1.9 N, about 2.0 N, about 2.1 N, about 2.2 N, about 2.3 N, about 2.4 N, about 2.5 N, about 2.6 N, about 2.7 N, about 2.8 N, about 2.9 N or about 3.0 N and sends out a signal. In some embodiments, the sensor only sends a signal at the onset of a sufficient force. The signal is not limited. In some embodiments, the signal is a mechanical signal or an electrical signal. In some embodiments, the sensor is a piezoelectric sensor which sends out an electrical signal. In some embodiments, the piezoelectric sensor measures a force of about 2 N and sends an output of about 2 Volts.

In some embodiments, the sensor increases or decreases in pressure and the pressure change is detected by a pressure gage.

In some embodiments, the signal indicator comprises electronic circuitry that processes a signal provided from the sensor. In some embodiments, the electronic circuitry will only provide a signal indication when a specific threshold of signal is met. In some embodiments, the electronic circuitry will provide an indication when the sensor provides a signal of at least about 2 volts. In some embodiments, the electronic circuitry will provide an indication when the sensor provides a threshold pressure.

In some embodiments, the sensor comprises electronic circuitry that will only provide a signal to the signal indicator when a specific threshold is met. The threshold is not limited and can be a specific voltage, electric current, or pressure. In some embodiments, the threshold is a voltage of 2 volts. In some embodiments, the threshold is a pressure. In some embodiments, the electronic circuitry is separate from the sensor and is provided with an input from the sensor.

In some embodiments, the device is in the shape of a cylinder and one end of the cylinder is connected to the signal indicator and the probe protrudes from the opposing end of the cylinder. In some embodiments, the device is in the shape of a cylinder and one end of the cylinder is connected to a light source as the signal indicator and the probe protrudes from the opposing end of the cylinder. In some embodiments, the device is in the shape of a cylinder and a display is on an exterior surface of the cylinder. In some embodiments, the device is in the shape of a cylinder and a pressure gage is on an exterior surface of the cylinder.

In some embodiments, the signal indicator provides an indication when the device is pressed against thyroid and/or cricoid cartilage but does not provide an indication when pressed against the cricothyroid membrane. In some embodiments, the signal indicator provides an indication when the device is pressed against cricothyroid membrane but does not provide an indication when pressed against the thyroid and/or cricoid cartilage. In some embodiments, the signal indicator provides a light when the device is pressed against thyroid and cricoid cartilage but does not provide a light when pressed against the cricothyroid membrane.

In some embodiments, the device provides a momentary indication when the device is pressed against thyroid and/or cricoid cartilage and a second momentary indication when the device is transitioned by sliding and is pressed against CTM. In some embodiments, the device does not provide an indication when the device is pressed against thyroid and/or cricoid cartilage but provides an indication when the device is transitioned by sliding to be pressed against CTM. In some embodiments, when the probe is transitioned by sliding from pressing on cartilage to pressing on CTM, the force provided by the temporary deformation and reformation of the CTM by the probe will trigger an indication by the signal indicator. In some embodiments, this indication is a light.

In some embodiments, the signal indicator is a pressure gage that provides a different pressure reading when the device is pressed against the cricothyroid membrane than when pressed against thyroid and cricoid cartilage. In some embodiments, the signal indicator is a pressure gage that only provides a signal when the device is pressed against a surface with a stiffness (elastic modulus) greater than or equal to a specified value.

In some embodiments, the device is able to detect the cricothyroid membrane +/−5.0 mm from the longitudinal and transversal neck midline. The average cricothyroid membrane dimensions are 12.4 mm longitudinally and 13.7 mm transversally (Dimensions of the laryngeal framework in adults Eckel, H. E., et al. "Dimensions of the Laryngeal Framework in Adults." Surgical and radiologic anatomy: SRA 16.1 (1994): 31-36). Therefore, being 5.0 mm apart from the midline would give some degree of error to the operator to make a proper incision. FIG. 1 shows a diagram of the longitudinal and transversal midlines with respect to the cricothyroid membrane and these accuracy parameters.

In some embodiments, accuracy is an aspect of the invention disclosed herein. Accuracy enables improvements in cricothyrotomy and survival rates of patients subject to cricothyrotomy. In some embodiments, the invention can enable the user performing a cricothyrotomy to avoid damaging the cricothyroid muscles, central cricothyroid arteries, cricoid and thyroid cartilages, vocal cords or thyroid. In some embodiments, accurate detection can be performed on patients 12 years old and older.

In some embodiments, the invention is portable with the capacity to be stored in the pocket and fit easily into an average human hand. In some embodiments, the device has a weight of <2 pounds. These functional attributes improve the operability of the device and increase the confidence of the operator.

In some embodiments, intermediate EMTs and health personnel with higher classifications can use the device successfully. In some embodiments, the invention is easy to use to a degree where Intermediate EMTs, such as EMT-I/85 or AEMT are able to use it. This functional attributes increases the possibility of unexperienced EMTs performing cricothyrotomies and successfully gain access to the airway.

In some embodiments, the invention can detect the cricothyroid membrane within seconds (e.g., 10-15 s). The speed of detection is a function of the operator skill and the speed of the sensor. The operator must be capable of using the device efficiently and quickly. Most sensors have a response time in the nano and microsecond level and the use of a piezoelectric sensor can contribute increasing the speed of detection.

The mechanical properties of the cricothyroid membrane and the thyroid and cricoid cartilages differ by orders of magnitude. The ablumenal superficial cartilage in the trachea and the vocal ligament have an elastic modulus of 13.6+/−1.5 MPa and 33.1+/−10.4 kPa, respectively (MIN et al., "Stress-strain response of the human vocal ligament." ANNALS OF OTOLOGY RHINOLOGY AND LARYNGOLOGY 104.7 (1995): 563-9. It is approximated that the vocal ligament and the CTM have similar mechanical properties.

In some embodiments, the device can exert a pressure equal or greater to 33.1+/−10.4 kPa. In some embodiments, the device can detect a pressure of about 33.1+/−10.4 kPa. In some embodiments, the device can exert a pressure of between 33.1+/−10.4 kPa and 13.6+/−1.5 MPa. In some embodiments, the device can detect a pressure of between 33.1+/−10.4 kPa and 13.6+/−1.5 MPa. In other embodiments, the invention can detect a pressure of about 13.6+/−1.5 MPa. In some embodiments, the pressure exerted by the cartilages is small in comparison to the external force created by the operator, therefore the invention can detect small variations in pressure.

In some embodiments, the sensitivity of the device is a function of the spring and piezoelectric sensor. The spring mostly is going to determine the force the device is capable of detecting. Hooke's law can be used to calculate the force detected by the device depending on the length of the spring and the spring constant. In some embodiments, the piezoelectric sensor is sensitive enough to translate the applied force by the tissues into the required voltage needed to light an LED. In some embodiments, both the sensor and spring are sensitive enough to detect a pressure of 13.6+/−1.5 MPa or of 33.1+/−10.4 kPa.

Seeing that most mistakes during an emergency cricothyrotomy occur in the field rather than a hospital setting, in some embodiments the device is portable in order for it to be practical. In some embodiments, the device is portable enough for use in tight spaces such as in ambulances and helicopters. Helicopters have a major issue with space and weight so for that reason portable ultrasounds are not practical. In some embodiments, the device is handheld in order for the operator to be able to handle the detector device in the same hand.

In some embodiments, the device's tip or probe, which is the one that is mostly going to be in contact with blood, can be easily sterilized with an antiseptic or antimicrobial agent, for example ethanol or VIRKON, or otherwise disposed. In some embodiments, the device can be left under UV light for 30 minutes or 1 hour or more and then flipped over for 30 minutes or 1 hour or more of UV light exposure.

In some embodiments, the invention is a portable, accurate, cost-effective pen-like device that is designed to accurately and externally detect underlying tissues in the human body. The principle of detection is the difference in stiffness of the target and surrounding tissues. In some embodiments, the device is always in contact with the skin and it profiles in a straight line across the surface.

Figure 2:
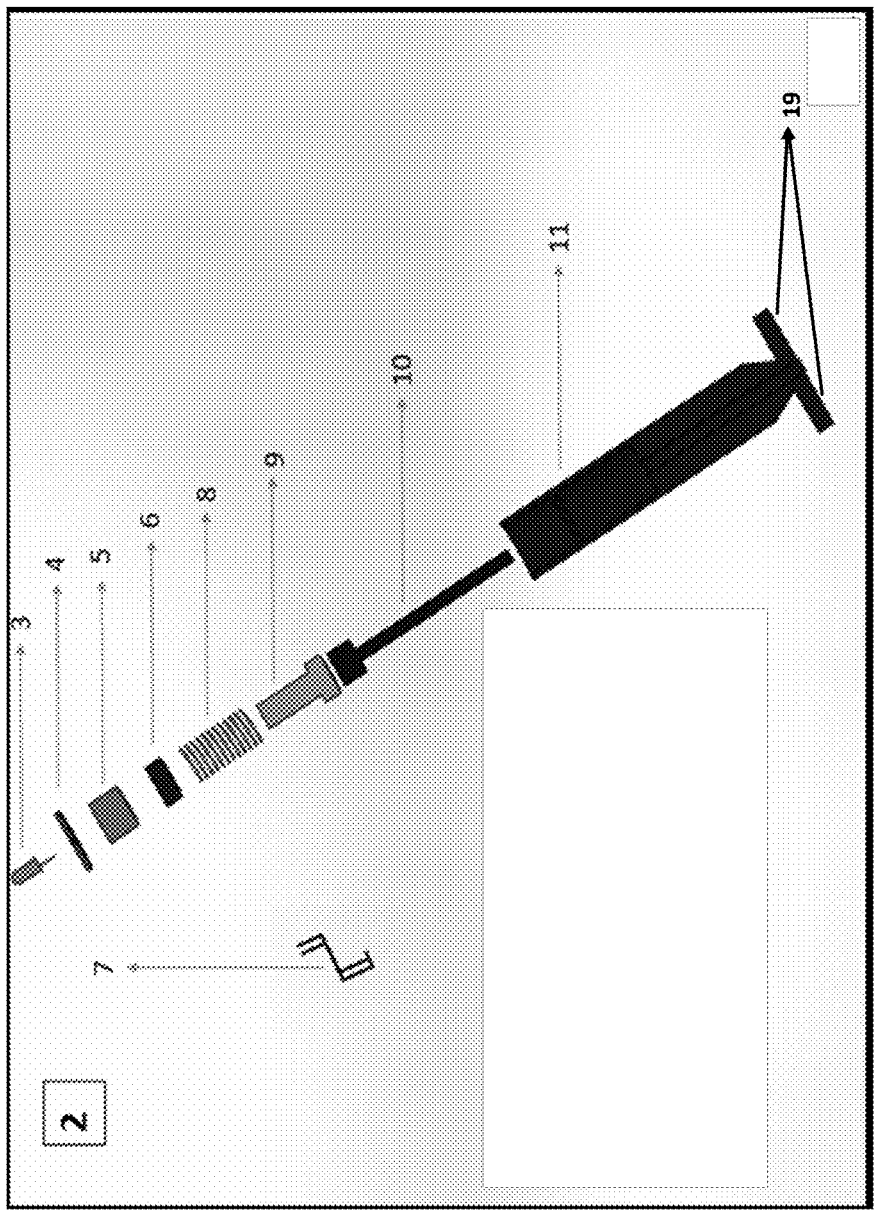
FIG. 2. An exploded view of an embodiment of the device. Light Emitting Diode (LED) (3), Cap (4), Cushion (5), Sensor and Integrated Circuit (IC) (6), Wires connecting Sensor/IC with LED (7), Spring (8), Spring Pin (9), Probe (10), Container (11) with two Horizontal Members (19).

FIG. 2 illustrates an exploded view of an embodiment of the device showing an LED signal indicator (3), Cap (4), Sensor and Integrated Circuit (IC) (6), Cushion (5), Wires connecting Sensor/IC with LED (7), Spring (8), Spring Pin (9), Probe (10), and Container (11).

Container (11) is a container which is a polymer pen-like structure that encases the components. Probe (10) is a polymer detection probe, which is in contact with the skin and it is connected directly to Spring Pin (9), which triggers the piezoelectric force transducer sensor (6). The piezoelectric force transducer sensor (6) converts the mechanical input into an electrical output (2 V), therefore when Spring Pin (9) knocks piezoelectric force transducer sensor (6), LED signal indicator (3) lights up.

In some embodiments of the configuration shown in FIG. 2, two or more tissues with similar mechanical properties and higher elastic modulus must surround the target tissue. The elastic modulus of the tissue is in units of pressure (Pascals), however because the sensing area is established, the relationship P=F/A can be used to calculate the force in Newtons necessary to activate the device. By knowing the force at which the sensor is activated, the desired spring constant can be derived from the Hooke's Law relationship for a spring constant. Hence, the device can be adjusted to any detection range. An example for the device detection mechanism is the cricothyroid membrane (CTM), which is a soft ligament with low elastic modulus that is surrounded by two hard hyaline cartilages (thyroid and cricoid, 13.6+/− 1.5 MPa) with identical mechanical properties. Therefore, under these conditions, the device will detect the cartilages and doing so will detect the CTM indirectly.

In some embodiments, the device is used to detect the cricothyroid membrane for cricothyrotomy. In some embodiments, the device facilitates the detection of the CTM in adults of both genders, improves survival rates, and decreases post-procedure complications including, but not limited to, hemorrhage, nerve damage and infection. In some embodiments, the device is used for the detection of different cartilages, ligaments and tendons in an infant's elbow, which compose a significant part of the elbow. These tissues are in close proximity and cannot be seen in an x-ray, which is a problem when fractures occur. Similarly, the knee joint contains four bones and is joined by two joints, five ligaments, three cartilages and muscle in close proximity, which without incision, can be difficult to identify. In some embodiments, the device is used to suggest locations to make surgical incisions or perform intraosseous infusions.

There may be inconsistent pressure applied by the operator of the device of the invention. Thus, in some embodiments, the invention further includes a separate base configured to be placed on the patient to reduce inconsistent pressure by the operator when sliding the device along the patient's skin. In some embodiments, the separate base is a concave member having a longitudinal slot that is placed over the neck with the longitudinal slot over the CTM and surrounding cartilage. The longitudinal slot has a width that is less than a width of a portion of the container or horizontal members thereof of the device but greater than a width of the probe. Thus, in some embodiments, the separate base prevents or reduces variations in force transmitted to the sensor when the user reduces or increases the force applied to the probe. In some embodiments, the base comprises a member that removably attaches to the device, wherein the member is set on tracks or wheels on one or more sides of the longitudinal slot of the base. In some embodiments, the base has tracks on either side of a slot that engage horizontal elements of the device. In some embodiments, the horizontal elements of the device comprise wheels or rollers that can engage with the base. In some embodiments, the use of the base and a device with horizontal elements prevents the device from moving side to side on the patient and prevents the operator from applying too much pressure.

The separate base can be any suitable configuration and can be made of any suitable material. In some embodiments, the separate base is plastic.

In some embodiments, the device is able to detect the cricothyroid membrane directly while eliminating the external applied force of the operator. In some embodiments, the device detects force generated by deformation and reformation of the CTM when the probe is transitioned from pressing against cartilage to pressing against CTM.

In one embodiment, the invention is directed towards a method of performing an incision comprising using the invention as described above to locate a tissue in a patient and then making an incision into or above the located tissue. In some embodiments, the tissue is CTM.

In some embodiments, the method comprises sliding the device along the midline of a patient's neck and locating cartilage tissue above and below the CTM and then performing an incision into the CTM. In some embodiments, the method comprises sliding the device along the midline of a patient's neck and locating the CTM and then performing an incision into the CTM. In some embodiments, the method further comprises placing the separate base on the patient's neck with the slot over the CTM prior to sliding the device over the CTM.

In some embodiments, the user places the device as described above on a patient's neck midline at any location above the sternal notch and presses down. Then, the user slides the device along the midline until the device provides an indication of CTM. In some embodiments, the indication is a light.

While the invention has been described with reference to certain particular examples and embodiments herein, those skilled in the art will appreciate that various examples and embodiments can be combined for the purpose of complying with all relevant patent laws (e.g., methods described in specific examples can be used to describe particular aspects of the invention and its operation even though such are not explicitly set forth in reference thereto).

EXAMPLES

Example 1

Figure 3:
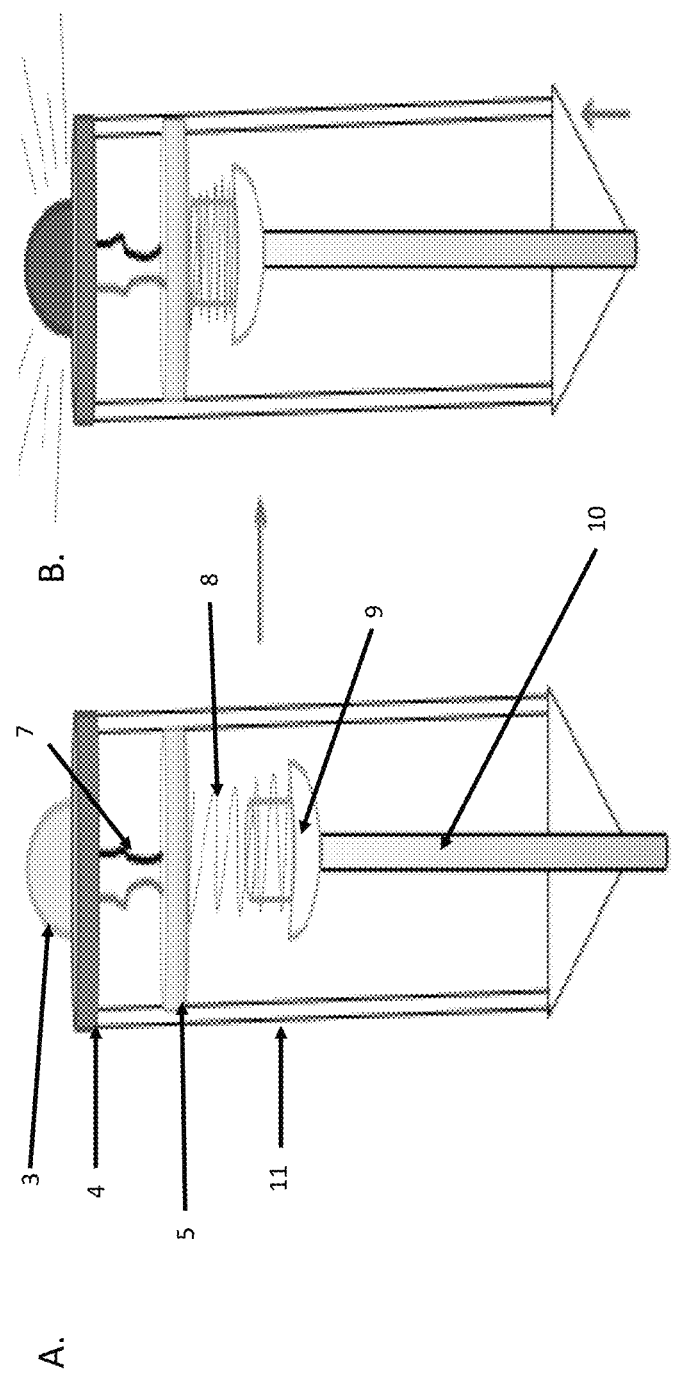
FIG. 3. Mechanism of an embodiment of the device. Panel A is a cutaway of a device of the present invention wherein insufficient force is applied to the probe (10) to trigger the LED signal indicator (3). Panel B is a cutaway of a device of the present invention wherein sufficient force is applied to the probe (10) to cause sufficient pressure on the sensor (6) by the spring pin (9) to produce a signal that lights the LED (3) signal indicator.

This example describes one embodiment of the invention. The device has a cylindrical design that will make it easy to use for the operator. The device has two plastic cylindrical elements (container and probe), one piezoelectric sensor, a spring and a LED light connected at the end. The combined electrical/mechanical approach involves the location of the cricothyroid membrane, which is located between the cricoid and the thyroid cartilages both having the same mechanical properties. It is based on a negative system. Since the cartilage's mechanical properties are known, the device is calibrated to detect the cartilage and membrane to cartilage transitions instead of detecting the membrane itself. One of the cylinders (probe) is inside the other cylinder and is hanging from a spring. This arrangement reduces the human variable when applying force. In addition, once the spring is compressed, the second cylinder presses onto the piezoelectric force transducer and transforms the mechanical movement into an output voltage. Consequently, the LED light turns on and therefore the user will know specifically where the membrane is (see FIG. 3).

Instructions

1. Patient is stabilized by laying him on the ground facing up.
2. Neck is exposed by lifting the chin of the patient.
3. The device is taken out of its packaging.
4. The device is pressed and slid along the midline of the neck going from top to bottom vertically.
5. Once the device touches the cartilage, the LED light turns on.
6. The device is continued to be slid along the neck until it turns off again (this where the membrane is).
7. The device is continued to be slid along the neck until it turns on again.
8. By doing that, the space where the membrane is located as the area between the two regions where the device is lit.
9. The user switches to a scalpel and makes an incision in the membrane area.

Figure 4:
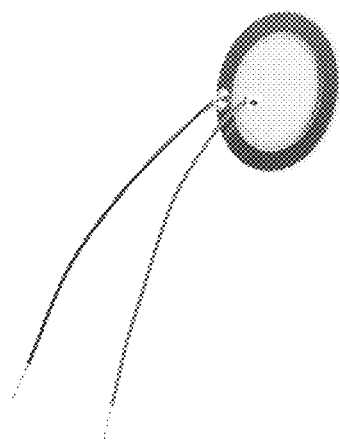
FIG. 4. Example piezoelectric force transducer sensor.

Materials
 Piezo Electric Sensor
  Sparkfun Electronics
  Sensing surface diameter
   0.010 m
  Load
   2 N
  Strain
   0.1%
 Spring
  Displacement
   0.006 m
  Spring Constant
   −293.06 N/m
  Stainless Steel wire
   12 coils
  Force
   1.76 N
 Cylinder
  Plastic
  LED light 2 Volts Engineering Feasibilities
Piezoelectric Force Transducer (FIG. 4)

This type of sensor transforms the mechanical energy in and outputs electrical signal, in this case a voltage. The sensor has a sensing area of 0.010 m as a diameter, resonant frequency 6.3+/−0.6 kHz, maximum resonant impedance (1000 ohms), capacitance 10.0+/−30% nF allow for the detection of the CTM. The amount of pressure needed to activate the sensor can be determined by the following equation, where F is the force needed to compress the spring without causing throat injury:

$$P = \frac{F}{A} = \frac{1.76\ N}{(0.0025^2 * \pi)} = 90\ kPa \tag{1}$$

Determining the pressure the sensor can detect itself is helpful when we compare it to the cartilage itself (13.6+/−1.5 MPa), which is three orders of magnitudes greater than the sensor. Thus, wherever the device is pushed against the cartilage, since it is stronger, it will push the spring pin towards the sensor and activate it. This principle considers that neither the skin nor the CTM exert a pressure larger than or equal to about 90×10³ Pa.

Spring

By knowing the force at which the sensor is activated, the desired spring constant can be derived from the Hooke's Law relationship for a spring constant:

$$F = -kX \tag{12}$$

$$k = \frac{F}{-x} = \frac{1.76\ N}{-0.006\ m} = 293.06 \frac{N}{m} \tag{13}$$

The spring of this example has 12 coils and a maximum displacement of 0.006 m. The wire width (diameter) in order to satisfy the spring constant relationship was determined using the following calculations:

$$k = \frac{Gd^4}{8nD^3} \text{ (Equation for the "spring constant")} \tag{14}$$

$$d = \sqrt[4]{\frac{8nD^3k}{G}} = \sqrt[4]{\frac{8*(12)(0.014)^3\left(29\frac{N}{m}\right)}{(7.722*10^{10}\ Pa)}} = 1.5\ mm \tag{15}$$

After calculating that, the parameters of the spring were set:
 Spring Constant (k): 293.06 N/m
 Shear Modulus of Steel (G): 7.722×10¹⁰ Pa
 Wire width (diameter): 0.001 m
 Diameter of the spring (D): 0.014 m
 Number of active coils: 12

In this example, the device will provide a light when pressed against cartilage but not when pressed against CTM. Thus, the user can identify the CTM by the absence of a light when the device is slid across the neck midline.

Example 2

This example describes another embodiment of the invention.

This embodiment functions by the differential pressure principle. The device contains a scalpel, balloon, spring, and a pressure gage. This mechanical approach detects the Cricothyroid Membrane since it is located between two cartilages (Cricoid and Thyroid) with different mechanical properties than the membrane. This design contains a separate base to decrease the amount of human error while applying pressure with the hand. This device consists of a differential pressure gage that can detect difference from 0-0.25 W.C (inches of water). (See FIGS. 5-7).

Figure 5:
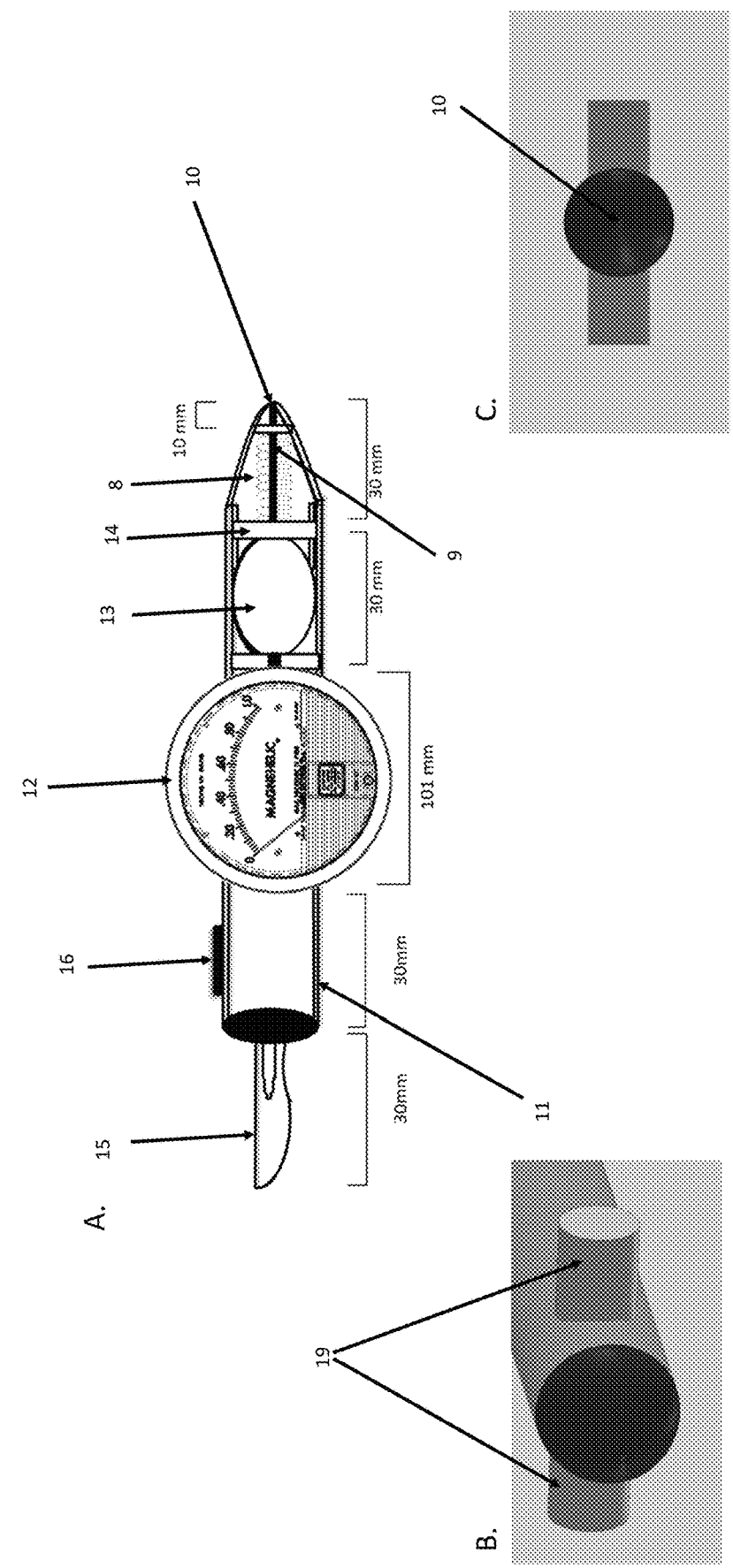
FIG. 5. Panel A is a partial cut-away view of another embodiment of the device showing Spring (8), Spring Pin (9), Probe (10), Container (11), Pressure Gage Signal Indicator (12), Balloon (13), Balloon Container Wall (14), Scalpel (15), and Scalpel Retraction Button (16). Panel B is a partial view showing horizontal members (19) at the end of the device near the probe tip. Panel C is an end view showing the probe tip (10).
Figure 6:
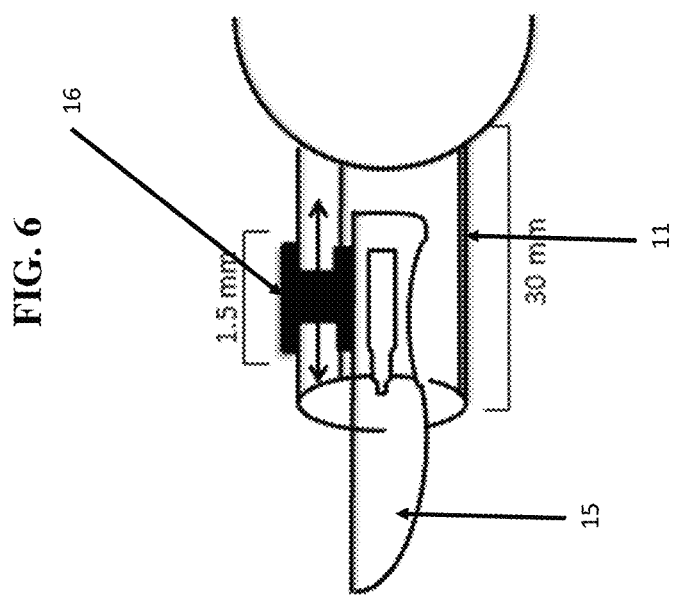
FIG. 6. Cut-away view of part of the device shown in FIG. 5. Scalpel Retraction Button (16) enables retraction of Scalpel (15) into the Container (11).
Figure 7:
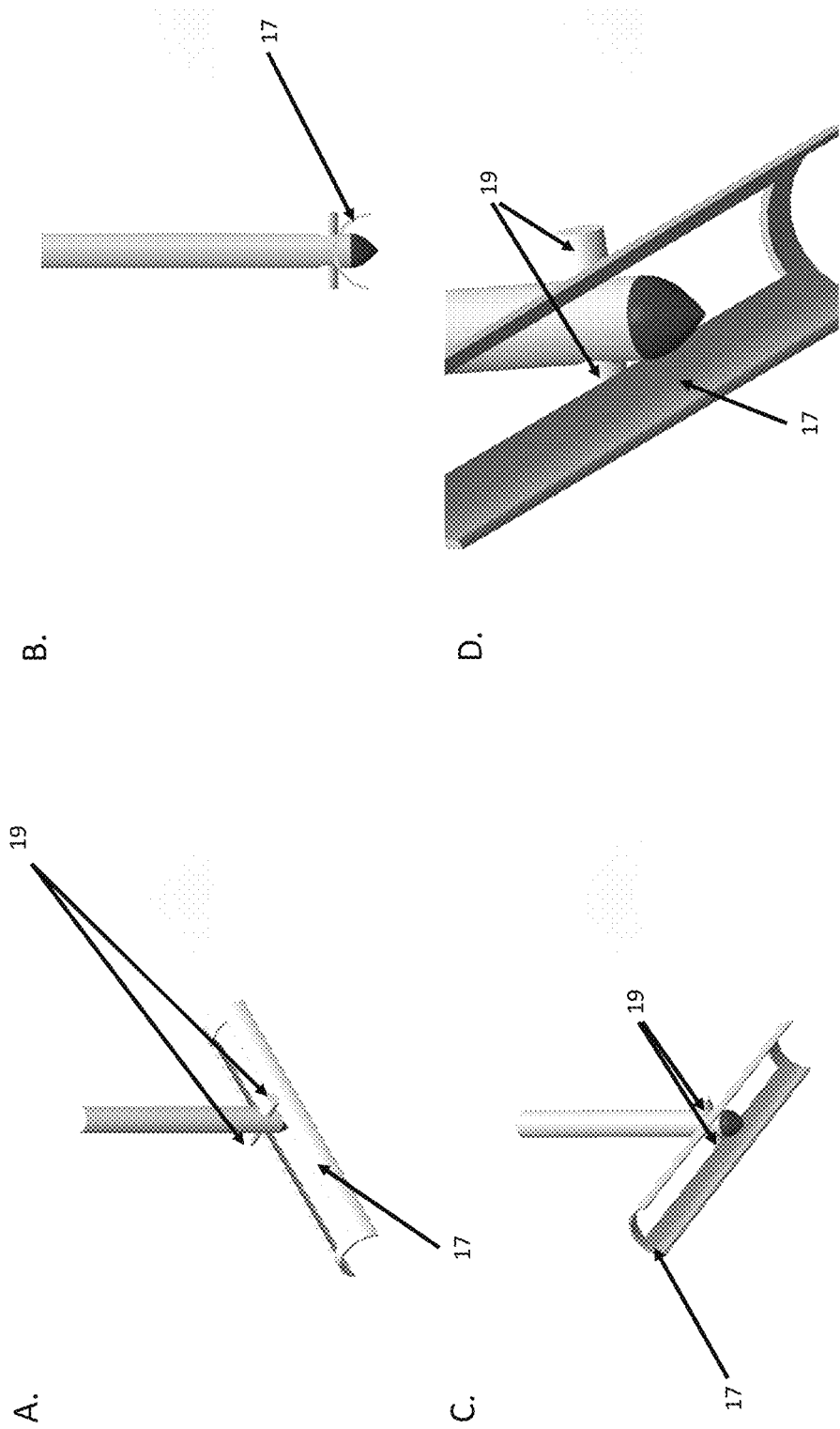
FIG. 7. Another embodiment of a device of the invention. Panel A is a top orthogonal view of a device of the invention having horizontal members (19) engaged with a slot in separate base (17) to decrease variations in pressure by the user. The device has horizontal members (19) that only allows a portion of the device to be inserted into a slot in the separate base. This decreases force variations caused by the user by isolating pressure on the probe tip caused by tissues of different hardness from pressure caused by the user varying how hard they press down. Panel B is a side view of the same device inserted into the base (17). Panel C is a bottom orthogonal view of a device of the invention having horizontal members (19) engaged with a slot in separate base (17). Panel D is a partial bottom orthogonal view of a device of the invention having horizontal members (19) engaged with a slot in separate base (17).

As shown in FIG. 5, Panel A, when force is applied to probe (10) it pushes on spring pin (9) that compresses spring (8) and then an end of spring pin (9) passes through balloon container wall (14) and presses on balloon sensor (13). Changes in pressure are indicated by pressure gage (12). As shown in FIG. 6, scalpel (15) can be retracted into container (11) when not in use. FIG. 7 shows an example wherein the device is inserted into a separate base (17) to decrease pressure variations caused by the user. The device in this figure has horizontal elements (19) that are wings that protrude from the side of the device and stop a portion of the device from passing through a slot in the separate base (17).

Instructions for Use:

1. Lay patient as still as possible in extended neck position or in supine position, if a spinal injury is evident
2. Carefully remove the device from its package 3. Place the half-cylinder base on the patient's neck with the slot in the base aligned with the longitudinal midline of the neck and over the Cricothyroid Membrane.
4. Open device's wings and insert the device end with the probe through the slot in the base. Adjust if necessary.
5. Slide the device across the region of the patient's neck having the membrane and cartilages
6. Observe the difference in pressure displayed on the Pressure Gage, the device is going to alert the operator when the device has reach the pressure difference threshold
7. Once the CTM is spotted, turn around the device and slide open the scalpel
8. Apply pressure to make an incision in the CTM Materials
  Scalpel
    No. 10
    Stainless Steel
    Shape: Curved
    Cutting Edge: 30 mm
    Thickness: 0.4 mm
  Differential Pressure Gage
    Brand: Dweyer Magnehelic
    Silicon Diaphragm
    Service: Air and non-combustibles
    Diameter: 101.6 mm
    Differential Pressure Range: 0 to 100 kPa
  Spring
    K=1180.33 N/m
    X: 22 mm
    F: −25.9 N
    Stainless Steel
    Number of Active Coils: 8
    Diameter: 14 mm
  Balloon:
    Polyethylene non-porous film
    Shape: Ellipsoid
    Volume: $9.17 \times 10^{-7}$ m$^3$ Engineering Feasibility
Balloon Pressure The pressure in the balloon will determine the amount of pressure difference marked in the gauge. The balloon has a volume of $9.17 \times 10^{-7}$ m$^3$ with an absolute pressure inside of 160,069 Pa. The volume was calculated with the formula of an ellipsoid since it's the form that the balloon will take once inside the device. As the balloon compresses by the force of the spring, the pressure inside the balloon increases and the gauge detects this change. The applied pressure on the balloon times the area is proportional to the applied force. The balloon is filled with air, which has a calculated mass of $1.76 \times 10^{-6}$ kg and has a molar mass of 0.0297 kg/mol. Thus, the pressure can be calculated from PV=nRT as follows.

$$P = \frac{\left(\frac{m}{M}\right)RT}{V} \tag{1}$$

$$P = \frac{\left(\frac{176*10^{-6} \text{ kg}}{0.0297 \frac{\text{kg}}{\text{mol}}}\right)\left(8.312 \frac{J}{K \text{ mol}}\right)(298 \text{ K})}{9.17*10^{-7} \text{ m}^3} = 160,069 \text{ Pas} \tag{2}$$

Compression Spring Constant

The spring constant is unique for every spring. For this device the spring constant (k) is 1180.33 N/m. This constant was calculated knowing that the spring was going to be made of stainless steel and the specific shear modulus for this material was found in literature. Also, these materials would have a high yield stress and yield strain. The spring will be made of 8 active coils giving a total of 10 coils. The mean diameter of the spring will be the same of the balloons, 14 mm. The wire is 1.28 mm thick since this allows the spring to store energy and provide a force or pressure.

$$k = \frac{Gd^4}{8nD^3} \tag{3}$$

$$k = \frac{(7.722*10^{10} \text{ Pas})(0.00128 \text{ m})^4}{8*8*(0.014)^3} = 1180.33 \frac{N}{m} \tag{4}$$

Hooke's Law: Spring's Force

The spring constant is necessary so that the force of the spring could be calculated. Since the cricothyroid membrane detection system of this embodiment will only be using compression and no elongation, the displacement (X) was assumed to be 22 mm. The spring displacement is 22 mm since the spring is originally 30 mm long (coiled) and each coil is 1 mm thick (8 active coils). Knowing the spring displacement and constant, the force was calculated and the result was −25.9 N.

$$F = -kX \tag{5}$$

$$F = -\left(1180.33 \frac{N}{m}\right)(0.022 \text{ m}) = -25.9 \text{ N}$$

Pressure Gage

The cartilages and cricothyroid membrane exert pressures of 13.6+/−1.5 MPa and 33.1+/−10.4 kPa, respectively. Therefore, the gage must be able to detect the change in pressure between the cricothyroid membrane and the maximum applied pressure by the balloon. The balloon itself provides with an absolute pressure of 160 kPa or a gauge pressure of 60,000 kPa. The fully compressed spring provides with an absolute pressure of 168 kPa or gauge pressure of 68 kPa. Therefore, the fully compressed spring will be able to compress the balloon, which will give a reading in the pressure gage of approximately 60,000 kPa. When the device is located over the cartilage and transitioned to the membrane, the gage is going to register a pressure difference of approximately 27 kPa. This pressure difference comes from the fully compressed state of the balloon and the release in pressure when it reaches the cricothyroid membrane.

An operator will thus make an incision in the neck at a portion between two areas wherein the reading on the gauge is 27 kPa (see FIG. 5—Magnehelic Pressure Gage). The device has markings in inches of water but it can be customized to any pressure units such as Pascals or Psi.

Spherical Tip

Even though there are a lot of forms of tips available in the market such as the Berkovich, cube corner, Vickers, wedge, cone, and many others, the spherical tip was the most adequate for the purposes of this design. One of the main advantages of using a spherical tip is the decrease in pressure to the patient's neck. The hardness of the spherical tip was calculated with this simple formula which is also equivalent to mean contact pressure (MCP). The MCP is the pressure at which the spring is going to compress. This pressure of 168 kPa is greater than the membrane pressure but lower than the cartilages. Therefore, the device will be able to detect the transition in the tissues. The main goal of the tip only to make enough pressure on the tissue of the patient to move the spring and not to make an incision.

$$P_m = H = \frac{4P}{\pi d^2} \tag{9}$$

$$P_m = H = \frac{4(-25.9 \text{ N})}{\pi 0.014 \text{ m}^2} = 168,772 \text{ Pa} \tag{10}$$

Mechanism to Apply Constant Pressure

It is desirable to decrease the human error while applying pressure to the patient. To solve this problem a half, hollow cylinder shape base is placed in top of the patient. The device has integrated "wings" that contain wheels for motion freedom. The half cylinder has tracks that allow the wheels from the wings to roll along the neck longitudinal axis. The half cylinder will allow for constant pressure since the "pen" cannot go further down than allowed. The interface of the wings and the base is exemplified in FIG. 7.

Example 3

This example describes another embodiment of the invention.

Container:

A polymer cylinder that contains the rest of the elements inside. A polymer rod probe hangs from a spring at one end and the other end extrudes from an end of the container. The spring reduces external human force variations by letting the probe slide along an inner contact surface of the outer cylinder. The length of the device is 132 mm total with a diameter large enough to keep the sensor in place.

Spring:

Made up of steel, it follows the material properties established in the ASTM standards. Since the shear modulus of steel is $7.722 \times 10^{10}$, the spring has a spring constant of k=293.06 N/m in order to balance the force exerted up by the cartilage and activation of the sensor. The spring has 12 coils, with a diameter of 0.014 m and wire thickness of 0.001 m.

Sensor:

The sensor converts the mechanical force into a signal output. The device has a piezoelectric sensor that converts mechanical force into an electrical signal. The sensor measures a 1.76 N force and sends an output of 2 Volts. The entire sensor has a diameter of 20 mm, with a sensing part having a diameter of 10 mm.

Light (Output):

The device has a 2V LED light at the end of the device connected to the piezoelectric sensor. This light turns on when it receives the electrical input provided by the sensor whenever it is pushed with sufficient force.

The device has a cylindrical design that will make it easy to use for the operator. This embodiment of the device consists of two polymer cylinders, one piezoelectric sensor, a spring and a LED light connected at the end. The combined electrical/mechanical approach involves the location of the cricothyroid membrane, which is located between the cricoid and the thyroid cartilages both having the same mechanical properties. The device detects the difference in mechanical properties between the cartilage and the cricothyroid membrane. Since the cartilage's mechanical properties are known, the device is configured to detect them instead of detecting the membrane itself. The configuration of having the probe hang from the spring decreases error caused by variations in external force applied by the operator. The LED will turn on when the device is pressed against the cartilage but not turn on when pressed against the CTM.

Figure 8:
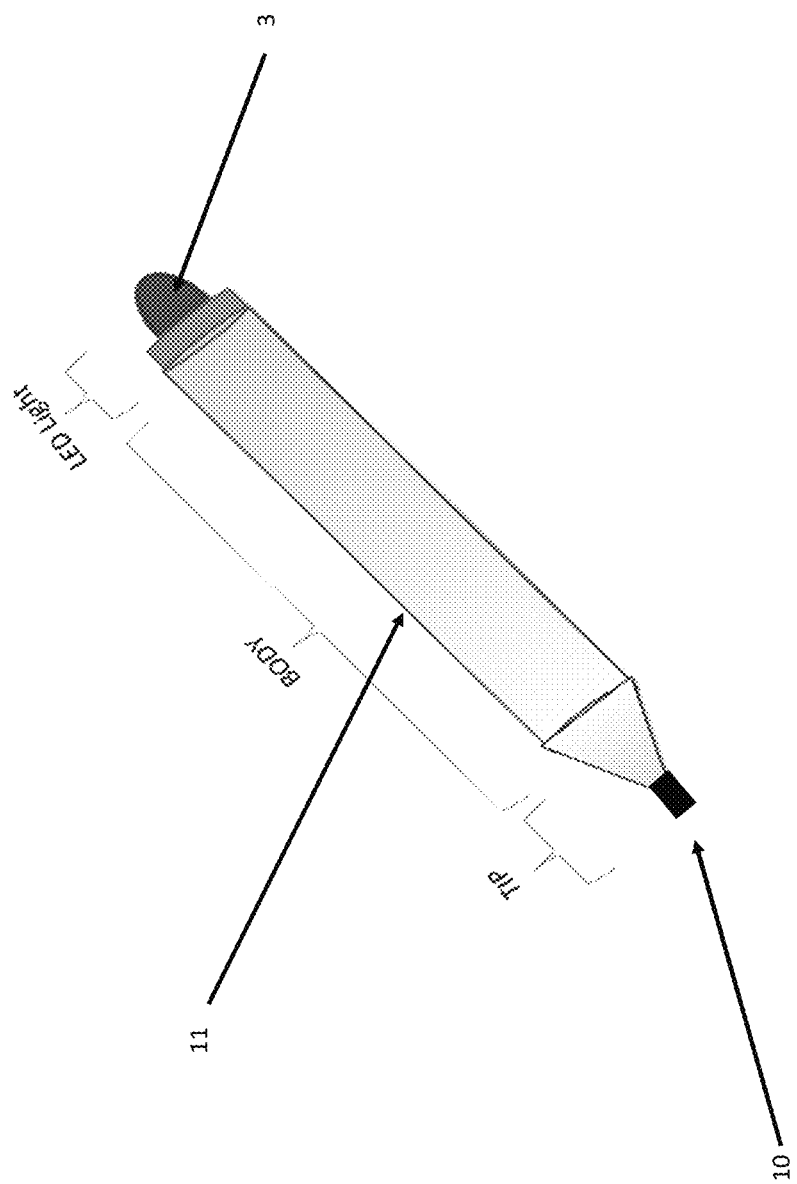
FIG. 8. Embodiment of the device of the invention with container (11), LED signal indicator (3) and tip of probe (10).

This device was analyzed and it was the one with the highest score in accuracy (5.0 mm+/−from the longitudinal and transversal neck midline), easiness of use (EMT-I/85), detection time <15 seconds, portability (<2 pounds) and sensitivity (33.1+/−10.4 kPa). FIG. 8 is an example of this device.

Engineering Feasibility

The way the piezoelectric sensor works is essential for this embodiment of the device. This type of sensor transforms the mechanical energy into an electrical signal, in this case a voltage. The sensor has a nominal load of between 1.5-2 N max for activation and a sensing area of 0.010 m as a diameter. The amount of pressure needed to activate the sensor can be determined by the equation, where F is the force needed to compress the spring without causing throat injury:

$$P = \frac{F}{A} = \frac{1.76 \text{ N}}{(0.0025^2 * \pi)} = 90 \text{ kPa} \tag{21}$$

Determining the pressure that the device can exert is helpful when compared to cartilage itself at 13.6+/−10.4 MPa, which is three orders of magnitude greater than the one of the sensor. Thus, wherever the device touches cartilage, since it is stronger, it will push the cylinder towards the sensor and eventually activate it. This principle considers that neither the skin nor the CTM exert a pressure larger than $90 \times 10^3$ Pa.

Spring

By knowing the force at which the sensor is activated, the desired spring constant can be derived from the Hooke's Law relationship for a spring constant:

$$F = -kx \tag{12}$$

$$k = -\frac{F}{x} = \frac{1.76 \text{ N}}{0.006 \text{ m}} = 293.06 \frac{N}{m} \tag{13}$$

Since the spring is intended to have 12 coils and a maximum displacement of 0.006 m, there has to be a change in the wire width (diameter) in order to satisfy the spring constant relationship. That was done doing the following calculations:

$$k = \frac{Gd^4}{8nD^3} \text{ (Equation for the "spring constant")} \tag{14}$$

$$d = \sqrt[4]{\frac{8nD^3 k}{G}} = \sqrt[4]{\frac{8*(12)(0.014)^3 \left(29\frac{N}{m}\right)}{(7.722*10^{10} \text{ Pa})}} = 1.5 \text{ mm} \tag{15}$$

After calculating that, the parameters of the spring were set:
Spring Constant (k): 293.06 N/m
Shear Modulus of Steel (G): $7.722 \times 10^{10}$ Pa
Wire width (diameter): 0.001 m
Diameter of the spring (D): 0.014 m
Number of active coils: 12

In this device, the LED will light when the device is pressed against cartilage but will not light when pressed against CTM.

Example 4

Figure 9:
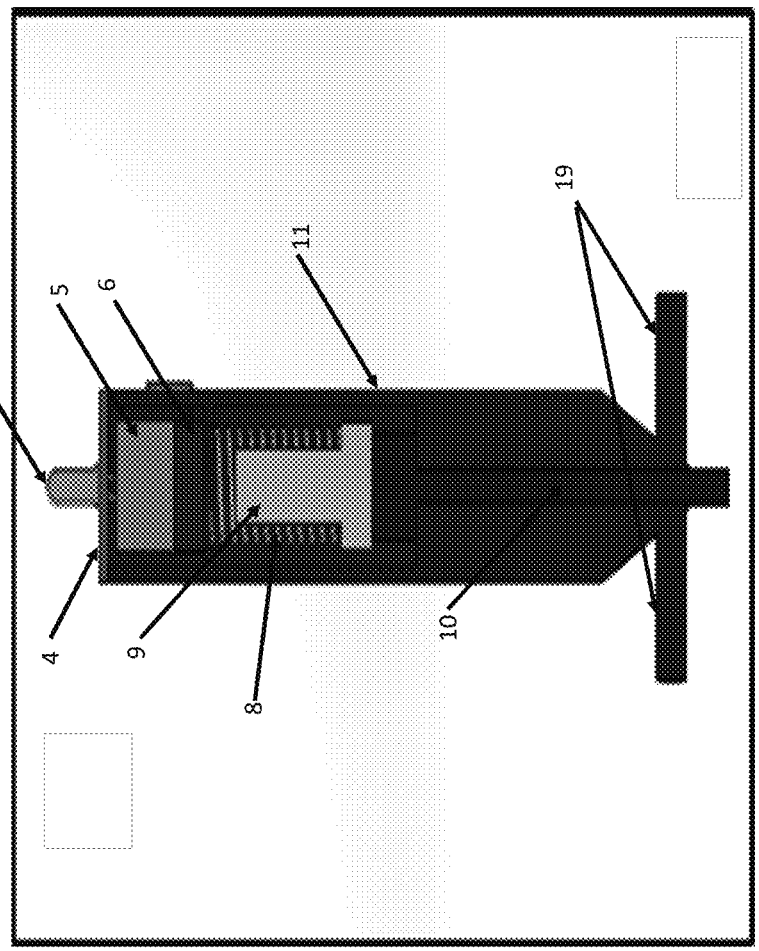
FIG. 9. Cut-away view of the assembled device of FIG. 2. LED signal indicator (3), Cap (4), Sensor and Integrated Circuit (IC) (6), Cushion (5), Spring (8), Spring Pin (9), Probe (10), Container (11) with two horizontal members at an end (19).

This example describes another embodiment of the invention. A cut away view of this embodiment is represented by FIG. 9.

Container: The container is a polymer cylinder that contains the rest of the elements inside. A polymer probe rod is placed inside the cylinder with one end at a determined distance from the sensor and the other protruding from the cylinder. The length of the device is 147 mm total with a diameter of 2.5 cm.

Spring: The spring is made up of steel, and follows the material properties established in the ASTM standards. Since the shear modulus of steel is $7.722 \times 10^{10}$, it has a spring constant of k=333.33 N/m in order to balance the force exerted up by the cartilage and activation of the sensor. The spring has 10.5 coils, with a diameter of 0.014 m and a wire thickness of 0.001 m.

Sensor: The device has a piezoelectric sensor (SEN-10293, Sparkfun) that converts force into an electrical signal. The force that the sensor can measure is of 2.0 N and the sensor can send an output of 2 Volts. The entire sensor has a diameter of 20 mm, with a sensing part diameter of 10 mm.

Light (output): A 2V LED light located at the end of the device is connected to the piezoelectric sensor. This LED will turn on when it receives an electrical input that is converted from the mechanical stimuli.

The device has a cylindrical design to make it comfortable to use. The device has one polymer container, one polymer probe, a spring pin, one piezoelectric sensor, a spring and a LED light connected at the end. The combined electrical/mechanical approach involves the location of the cricothyroid membrane, which is located between the cricoid and the thyroid cartilages both having the same mechanical properties. The calibration of the device requires to intentionally compress the spring and keep it that way throughout the screening process. When the device reaches the membrane, the force of the spring will momentarily decompress against the softer tissue but then will re-compress again due to the operator force. This recoil-like movement in the transition from the cartilage to the membrane is what allows detecting the latter. Once the spring is compressed and decompressed, it will activate the piezoelectric force transducer and this will transform the mechanical movement into an output voltage. Consequently, that will cause the LED light to turn on and therefore the user will know specifically where the membrane is.

This device has high accuracy (5.0 mm+/−from the longitudinal and transversal neck midline), easiness of use (EMT-I/85), detection time <15 seconds, portability (<2 pounds) and sensitivity (33.1+/−10.4 kPa).

Engineering Feasibility.

The piezoelectric sensor transforms the mechanical input to an electrical signal output. The sensor has a nominal load of between 1.5-2 N max and a sensing area of 0.005 m as a diameter. The amount of pressure needed to activate the sensor can be determined by equation 1 where F is the force necessary to compress the spring without injury to the neck tissues.

$$P = \frac{F}{A} = \frac{2.0 \text{ N}}{(0.0025^2 \text{ m} * 3.14)} = 1019100 \text{ Pa} = 102 \text{ kPa} \tag{22}$$

Spring pressure and force relationship with an established diameter of 0.005 meters.

Determining the pressure exerted by the sensor is helpful when compared to the elastic modulus of the membrane (33.1+/−10.4 kPa). There is a difference of approximately 70 kPa between the membrane and the pressure exerted by the device. Hence, it can be concluded that the spring in the device will have the enough force or pressure to deform the cricothyroid membrane to some extent. This deformation of the membrane will lead to a compression and decompression of the spring which will stimuli the sensor and transduced to the LED. Therefore, it is needed to know the type of spring needed and define the parameters of the same. This principle considers that the skin and the CTM can be deformed and displaced at some extent with an applied force of 2.0 N or a pressure of 102 kPa.

Spring

By knowing the force at which the sensor is activated, the desired spring constant can be derived from the Hooke's Law relationship (equation 2) for a spring constant (the team is trying to use a similar spring to the previous design concept):

$$F = -kX \tag{2}$$

$$k = \frac{F}{X} = \frac{2.0 \text{ N}}{-0.006 \text{ m}} = 333.3 \frac{N}{m} \tag{3}$$

Since the spring has a diameter of 0.001 m and a maximum displacement of 0.006 m, there has to be a change in the number of coils in order to satisfy the spring constant relationship. That was done using the following calculations:

$$k = \frac{Gd^4}{8nD^3} \text{ (Equation for the "spring constant")} \tag{4}$$

$$n = \frac{Gd^4}{8kD^3} = \frac{(7.772 \times 10^{10} \text{ Pa} * 0.001^4 \text{ m})}{\left(8 * 333.3 \frac{N}{m} * 0.014^3 \text{ m}\right)} = 10.5 \text{ coils}$$

After calculating that, the parameters of the spring were set:

Spring Constant (k): 333.3 N/m

Shear Modulus of Steel (G): $7.722 \times 10^{10}$ Pa

Wire width (diameter): 0.001 m

Diameter of the spring (D): 0.014 m

Number of active coils: 10.5

This spring is resting on the spring pin. The spring force deforms the membrane leading to a mechanical input on the sensor surface and an output signal of 2.0 V, which in turn lights the LED.

1. Components

LED Basic Green—
  COM—09650 ROHS
Piezo Element—
  SEN-10293 ROHS
  Measurements: 20.0 mm diameter
Ultra High Molecular Weight Polyethylene—

2. Assembly Instructions

The lathe, Hardinge Super-precision Acu-rite III (HEIDENHAIN Corp., Schaumburg, Ill.), is used in the construction of the device.

Pre-Manufacturing Instructions
1. A UHMW polyethylene cylinder with a diameter the same size as the outer shell of the container (20 mm) is used as the bulk material.
2. A collet (clamp that forms a collar around material) of size 1/32 is used to hold the polymer material.
3. Insert the polymer tube inside the collet and the latter inside the lathe, holding it tightly and leaving enough plastic outside in order to work with it correctly.

Manufacturing Sequence
  Manufacturing probe and spring pin: Takes off the excess material by reducing their diameter to the desired dimension by utilizing a cutting tool attached to the lathe.
  Manufacturing container: An UHMWPE 20 mm tube is used and placed inside the 13/64 collet for holding. Cutting tool is used to get the desired dimensions according to engineering drawings.
  The bottom part of the container called the "tip" is worked first. A 25 mm UHMWPE tube is inserted and by starting the lathe, a hole is drilled with a 13/64 drill bit. It has to be deep enough to open a space for the probe to move through. The operator then uses a metal file to give a conical shape to the tip of the device. A hole is made perpendicular to the device on the conical tip to make space for the supports (19) on the bottom. After this is done, the collet is loosened and the container is reversed so the tip is held within the collet. Now, a 9/16 drill bit is used to bore a hole for the spring pin and then followed by a 5 1/64 drill bit to make space for the sensor. At the end, a parting tool is used to cut the material and give the device the desired length.

Assembly
  Insert probe into container until it reaches a stop.
  Insert spring pin so its head rests on the probe top.
  Insert spring and let it rest on spring tip.
  Place sensor and then cushion in container after spring.
  Place cap at the end of container and seal the entire device.
  Connect wires and LED.

Test for Correct Assembly
  Once the inside parts of the device are assembled, the operator makes contact and presses on any surface to check for the rod to come back out again. If the rod does not come out again on the tip, that means the spring was not placed properly and needs to be fixed.
  After the entire device is assembled, the operator presses on any surface again and checks for the LED light to turn on. If it does not turn on, that means the wires are not well connected or the pin is not making contact with the sensor.
  1. Double check wire connections
  2. Disassemble top part of device and double check that spring and pin are aligned in position with the rod.

3. Electrical Subsystem

TinyLily Mini Processor Model ASM2101 (Tinycircuits, Akron, Ohio). (FIG. 11). This microcontroller connects and provides enough voltage to the piezo element and LED.

The piezo element is connected to analog pin A0 and ground (GND) with a 1 MΩ resistor. The LED is connected to default pin 13 and ground. A 9 Volt battery source provides power to the microcontroller.

This IC was programmed using Arduino 1.6.3 Software and the following Open Source code was used:

```
const int LED = 13;
const int KNOCK = 0;
void setup( )
{
  pinMODE(LED,OUTPUT);
  Serial.begin(9600);        //use the serial port
}
void loop( )
  {
    int value = analogRead(KNOCK);
    if (value>100)
  {
    digitalWrite(LED, HIGH);
        Serial.println("LED on");
  }
  else
  {
    digitalWrite(LED, LOW);
  }
  delay(100);
}
```

The size of the piezoelectric element (FIG. 11) fits snugly within the dimensions of the device. It is integrated by letting it sit on a knob on top of the spring and is encapsulated in a water-proof container. The water-proof container serves to hold the sensor in place so it doesn't affect the sensitivity of the device. The cushion is placed above the sensor and absorbs the impact of the spring pin on the sensor to avoid damage to the device. The cushion also fills the gap between the container cap and the sensor.

4. Part Dimensions

Shape of Parts is Approximately Shown in FIG. 2

Container Shell: 25 mm external diameter; 20 mm internal diameter; 147 mm length Horizontal supports: 40 mm length; 0.5 mm diameter; inserted through hole near tip of container Probe: 81 mm length, 14 mm wide at end contacting with spring pin; head has depth of 10 mm; 71 mm body with a diameter of 0.5 mm Spring pin: 31 mm length, 10 mm wide at end contacting with spring; 16.5 mm wide with a length of 7 mm at head connecting with probe head Cap: 2 mm thickness; 20 mm diameter Sensor: 17 mm diameter; 7 mm thickness Spring: 14 mm diameter; 30 mm length; 1 mm diameter wire

Example 5

The following examples provides testing of an embodiment of the invention.

1. Sensitivity

Based on Hooke's law, which takes into account the spring constant and the displacement to determine the applied force, an embodiment of the invention was tested wherein the LED theoretically lights when ~2.0 N are applied to the device and there is a displacement of the spring of 6.0 mm.

This test was conducted in order to show that the sensor and circuit would work in sync to light the LED at the appropriate applied force. In this embodiment of the invention, the LED should only light up when the probe is transitioned from the cartilage to the CTM. Thus, it is important that the LED doesn't light on the cartilage.

Materials:
    Mark-10: Model MG05 force probe (Mark-10 Corporation, Long Island, N.Y.)
        Flat grip—G1025, 200 N.
    Caliper/Ruler
    Cricothyroid membrane detector Characteristics/Procedure:
Testing Conditions
    Sensing load on the device: 0-2.0 N
    6.0 mm displacement
    Temperature: 21° C.
    Atmospheric pressure: 1.0 atm
    Humidity: N/A
    Air flow: Laminar <2100 (Reynolds number)
    Variables:
        Testing subjects: Non-deformable flat surface
        Force supply: Operator
        Detector: Mark 10: Model MG05 force probe
        Type of test: Static compression test Data Recording
    Distance traveled by the probe and the forces produced are displayed on the probe screen. These were recoded into excel to get a correlation between average force vs. distance.

Test Evaluation
    Test Criteria
        The LED on the device must light on at an applied force of 2.0 N and it must be off at <2.0 N.
        In case the device doesn't light at 2.0 N, a higher force is going to be applied until the LED lights on.
    Test Tolerance
        Compression force +/−0.5 N.
        Displacement +/−0.5 mm
    Data Reduction
        Manual collection
            Plot of force vs. distance
    Excel spreadsheet
    Device shows peak values at each stage
    Statistical Analysis
        Average and standard deviation (SD) of applied forces (N=18).

Test Procedure
    This testing was divided into two parts: periodical and continuous force.

Figure 12:
FIG. 12. Experimental set up for testing sensitivity of invention to force applied to probe.

First Part: Periodical Device Force:
1. Set the Mark-10-MG05 against a flat surface with flat grip G0125. The force probe is set-up for compression test showing only peak values. The testing set up is shown in FIG. 12.
2. Set cricothyroid membrane detector device on flat grip.
3. Press the device in increments of 1.0 mm (6.0 mm max), while recording the force and the distance the device spring is compressed.
4. Repeat 18 times Second part: Due to the nature of the sensor, the probe must impact the piezo element in order for the LED to light on. Therefore, in order to obtain maximum recorded force, the device must be pressed continuously until the LED lights on.
5. Press the device continuously until the LED lights up, record max force (N),
6. Repeat 18 times
7. Calculate average force and standard deviation, Plot Force vs Distance in order to get the experimental spring constant.

Results/Discussion

Figure 13:
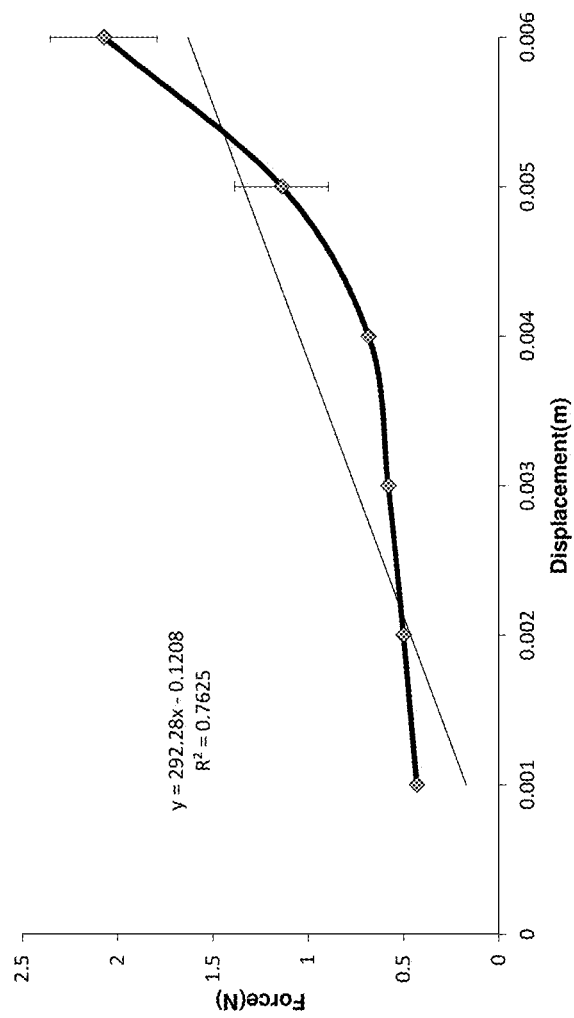
FIG. 13. Graph of Force vs. Displacement to determine the spring constant with average force values (N=18). Curved line indicates spring displacement (x-axis) versus force in Newtons (y-axis). Straight line corresponds to idealized values with a spring constant of k=292.28 N/m.

The purpose of this test was to determine the experimental detected force of the device and its spring constant in order to compare it with theoretical data. This was done by measuring the force exerted by the spring at 1.0 mm increments. Recording the peak force values at each increment from 0 to 6.0 mm, and plotting them on a force vs. displacement graph resulted in a linear trendline with an $R^2$ value of 0.75. The experimental spring constant was 292.28 N/m. There was a percent error of 12.3% for the theoretical spring constant of 333.30 N/m at 2.0 N. The relatively large percent error may have been due to the human factor. The force was applied by the operator instead of a compression machine such as MTS Insight 5 Criterion compression system. Nevertheless, this testing was enough to proof the proper functionality of the device with the proposed theory. FIG. 13 shows the force vs. displacement graph including all average periodical values (N=18).

Due to the nature of the piezo element sensor, the LED will only light on under probe impact instead of only smooth displacement; therefore the maximum peak force could only be detected through continuous displacement and impact with the sensor. In this manner, the obtained maximum average force was 2.07+/−0.28 N. Table 1 shows the overall data (N=24) for this test. This result has only a percent error of 3.5% for a theoretical value of 2.0 N.

TABLE 1

| Continuous Test overall data (N = 24). Continuous Test Displacement: 6.0 mm | |
|---|---|
| Test 1 | 1.728 |
| Test 2 | 1.820 |
| Test 3 | 1.948 |
| Test 4 | 1.630 |
| Test 5 | 2.400 |
| Test 6 | 2.612 |
| Test 7 | 2.372 |
| Test 8 | 2.684 |
| Test 9 | 2.348 |
| Test 10 | 2.116 |
| Test 11 | 2.108 |
| Test 12 | 1.940 |
| Test 13 | 2.184 |
| Test 14 | 1.884 |
| Test 15 | 1.838 |
| Test 16 | 2.096 |
| Test 17 | 2.082 |
| Test 18 | 1.972 |
| Test 19 | 1.978 |
| Test 20 | 1.714 |
| Test 21 | 2.302 |
| Test 22 | 2.286 |
| Test 23 | 1.782 |
| Test 24 | 1.936 |

TABLE 1-continued

Continuous Test overall data (N = 24).
Continuous Test Displacement: 6.0 mm

| | |
|---|---|
| Average | 2.073 |
| STEDEV | 0.280 |

Testing Constraints
  Manual operation of the device
  Precision was limited to 1.0 mm
  Ruler used to measure probe distance instead of software.
Conclusion These preliminary tests show that the device works on the principles it is intended to. However, only the continuous test with an average force of 2.07+/−0.28 at 6.0 mm was within the proposed statistical tolerance of 5.0%. As stated above, the large percent error is attributed to the human error. The experiment also introduced the concept of increasing the sensitivity within the sensor by increasing the probe size or decreasing spring compression.

2. Accuracy

Accurate anatomic localization of the cricothyroid membrane (CTM) is of critical importance for the success of emergency cricothyroidotomy. Aslani et al show a 20% and 60% correct identification of the cricothyroid membrane in obese and non-obese subjects, respectively. These results exemplify the inaccuracy of current detection methods and therefore, some embodiments of the present invention are designed to detect the membrane with at least 90% accuracy. In order to proof this concept, the membrane was detected using an embodiment of the invention in fifteen subjects of different genders. The control for this experiment was a portable ultrasound with a soft tissue probe.

The first part of testing was recording age, gender, cricothyroid membrane length, BMI (height and weight) for each subject. For simplicity of the test, BMI wasn't considered within the factors that affected the sensitivity of the device. Each subject was laid on a horizontal bench for the detection of the CTM in hyperextended position, using the detection device. A portable ultrasound for soft tissue was used to verify the true position of the membrane. All the data was manually inputted for analysis.

Materials:
  Sonosite m-turbo (SonoSite Inc., Bothell, Wash.)
  Soft Tissue Linear Probe 6-13 MHz
  Caliper/Millimeter Ruler
  Skin Marker
  Cricothyroid membrane detector
  Characteristics/Procedure:
  Testing Conditions
  Sensing load on the device: 0-2.0 N
  Temperature: 21° C.
  Atmospheric pressure: 1.0 atm
  Humidity: N/A
  Air flow: Laminar <2100 (Reynolds number)
  Variables:
    Testing subjects: Female and Male 18-50 yrs. (N=20)
    Hyperextended neck position
    Practitioners: Medical uncertified and untrained personnel with only device training (N=4)
    Sensing area is in the midline of the neck going from the sternal notch to the thyroid cartilage
    Detection Time: Unlimited
    Force supply: Operators hand
  Control: Ultrasound with soft tissue longitudinal/linear probe (6-13 MHz)
  Data Recording
    Data was manually collected and inputted into an excel spreadsheet when the LED lights up to identify the location of the cricothyroid membrane. The control, portable ultrasound device, was used to indicate whether or not the device was correct or incorrect in identifying the cartilages. Successes and failures were assessed visually and scored on an excel spreadsheet.
  Test Evaluation
  Test Criteria
    Correct identification of CTM within one half of longitudinal CTM size. Results verified with an ultrasound for true position of the membrane.
    Pass/Fail. If the LED lights on the membrane, the test will be passed, however there might be a scenario where the LED won't light up.
    Not time frame for identification.
  Test Tolerance
    80.0 to 90.0% successful identification in female and male subjects.
    +/−½ total membrane size of longitudinal CTM membrane
    0.0 to 2.0 N loading force
  Data Reduction
    Manual collection
      The ultrasound detection matches the prototype with an 80% successful identification
    Statistical Analysis
      Average and standard deviation (SD) for CTM length and lower boundary measurement with respect to cricoid cartilages.
      Average and SD from patient characteristics divided into women and men patients.
  Testing Procedure
  1. Record age, gender, CTM length (using ultrasound) and calculate BMI for each subject.
  2. Lay subject on a horizontal bench having the neck on hyperextended position.
  3. The operator will use the cricothyroid membrane detector probe and he will slightly press until the LED lights on for the first time, then drag the probe against the subject, maintaining the device engaged, along the neck midline and going from the sternal notch to the thyroid cartilage, respectively.
  4. The region where the LED lights on will be marked by the operator and this will show the location of the membrane.
  5. The ultrasound is going to be used on the subject to detect the true position of the CTM. The ultrasound is also going to be used to determine the longitudinal size of CTM.
    a. If time allows, steps 3-6 are repeated on the same subject with a different device operator.
  6. The subject is now able to stand
  7. Recorded data is statistically analyzed.

Figure 14:
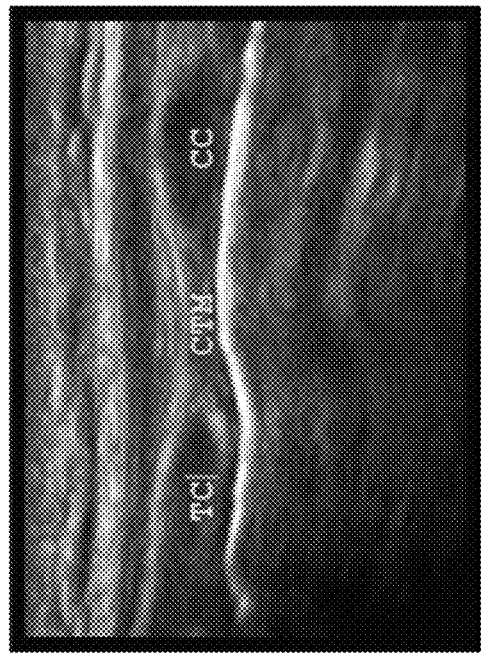
FIG. 14. Longitudinal view of the cricothyroid membrane (CTM), thyroid cartilage (TC) and cricoid cartilage (CC) obtained by ultrasound.
Figure 15:
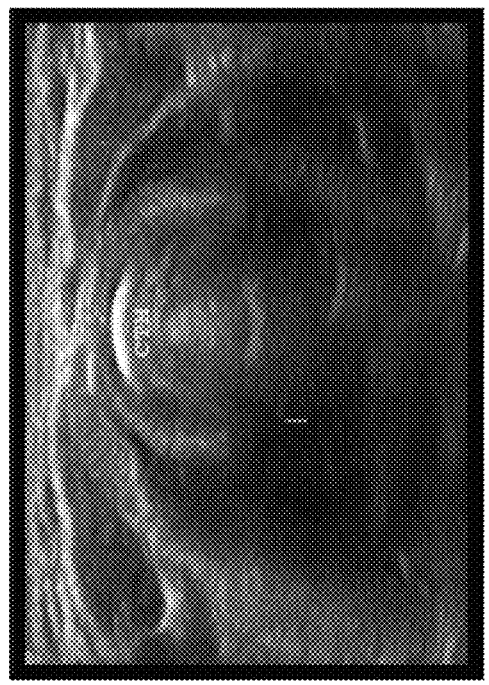
FIG. 15. Transverse view of the cricothyroid membrane (CTM) obtained by ultrasound.
Figure 16:
FIG. 16. Test set-up on male subject that is in hyperextended position with embodiment of the invention.

FIGS. 14 and 15 show the ultrasound longitudinal and transversal views of the cricothyroid membrane and its surroundings. FIG. 16 shows the test-set up on a male subject that is in hyperextended position. FIG. 16 shows how the device starts in compressed/engaged position right above from the sternal notch.

Results/Discussion

The CTM dimensions changes considerably between genders, therefore this test was divided into two sections: combined population and gender. The combined population for this test was 20 subjects from which 15 were male and 5 were female. There were two evaluation criteria: Pass/Fail and ½ total CTM longitudinal size. Detecting the membrane (LED lights on and ultrasound confirms the position of the CTM) within the two three attempts was considered as passing, and it was considered failure after the third. In the case of ½ the total longitudinal CTM size was from the way the device works. The device is able to detect the difference in pressure between the cartilages and the membrane. Therefore, as soon as the device probe leaves the cartilage, the LED will light on, indicating that the beginning of the membrane is detected and the incision can be done.

Table 2 displays the longitudinal CTM dimensions and low-midpoint distance for the combined population which includes 15 male and 5 female subjects. Subjects 13 through 16 were considered failures and therefore they weren't included in the table. The average low-midpoint distance and CTM length were 6.8+/−2.4 mm and 14.9+/−4.0 mm From this, it is shown that the device is detecting the membrane approximately from the edge; right as the device passes over the cricoid cartilage and strikes the membrane. This can be seen given that the distance between low-midpoint and the detected size is less than half of the average CTM size. Since the device travels down the longitudinal midline, the transversal distance was neglected. The percent accuracy for the device in the combined population (N=20) was 80.0% or 16 out of 20 successful identifications. This value matches our test tolerance of 80.0 to 90.0% accuracy and it is certainly an improvement to palpation which has shown lower accuracy percentages in certain studies.

TABLE 2

Distance from midpoint and CTM size in combined population (N = 20). Combined Population(N = 20)

| Subject | Low-mid(mm) | CTM dimsensions(mm) |
| --- | --- | --- |
| 1 | 7.5 | 16.6 |
| 2 | 4.5 | 17.4 |
| 3 | 13.7 | 23.3 |
| 4 | 7.9 | 15.5 |
| 5 | 9.0 | 18.1 |
| 6 | 7.2 | 16.3 |
| 7 | 7.2 | 17.3 |
| 8 | 8.5 | 18.0 |
| 9 | 7.8 | 18.2 |
| 10 | 6.0 | 14.0 |
| 11 | 5.0 | 12.0 |
| 12 | 6.3 | 12.0 |
| 17 | 5.1 | 7.9 |
| 18 | 4.5 | 10.0 |
| 19 | 4.2 | 11.2 |
| 20 | 5.2 | 10.2 |
| Average | 6.8 | 14.9 |
| STDEV | 2.4 | 4.0 |
| Accuracy(%) | 80.9% | |

**Note:
Subjects 13-16 were classified as failure due to inability of the device to detect the membrane.

Table 3 displays the average values for CTM dimensions and low-midpoint for the male population (N=15, 18-43 years). The average low-midpoint distance and CTM size was 7.1+/−1.5 mm and 15.7+/−2.4 mm, respectively. The accuracy of detection for N=15 male was 80.0%. Subjects 13-15 were classified as failure due to inability of the device to detect the membrane.

TABLE 3

Distance from midpoint and CTM size in male population (N = 15). Men(18-43 year)

| Subject | Low-mid(mm) | CTM dimensions(mm) |
| --- | --- | --- |
| 1 | 7.5 | 16.6 |
| 2 | 4.5 | 17.4 |
| 3 | 9.0 | 18.3 |
| 4 | 7.9 | 15.5 |
| 5 | 9.0 | 18.1 |
| 6 | 7.0 | 14.2 |
| 7 | 6.8 | 13.9 |
| 8 | 8.5 | 18.0 |
| 9 | 7.8 | 18.2 |
| 10 | 6.0 | 14.0 |
| 11 | 5.0 | 12.0 |
| 12 | 6.3 | 12.0 |
| Average | 7.1 | 15.7 |
| STDEV | 1.5 | 2.4 |
| Accuracy(%) | 80.0% | |

**Note:
Subjects 13-15 were classified as failure due to instability of the device to detect the membrane.

Table 4 displays the average values for CTM dimensions and low midpoint for the female population (N=5, 18-23 years). The average low-midpoint distance and CTM size was 4.2+/−1.4 mm and 8.7+/−2.6 mm. The accuracy of detection for N=5 was 75.0% percent. Subject 16 was classified as a failure due to inability of the device to detect the membrane. This part of the test didn't meet our accuracy passing criteria of 80%. The lack of accuracy can be attributed to the smaller size of the membrane in women and for the relatively blunt rod used in the prototype. During the testing stage, the prototype had a wheel-like structure that eased the movement of the device along the neck. Making this structure smaller should lead to improved sensitivity of the device.

TABLE 4

Distance from midpoint and CTM size in female population (N = 5) Women(18-30 years)

| Subject | Low-mid(mm) | CTM dimensions(mm) |
| --- | --- | --- |
| 17 | 5.1 | 7.9 |
| 18 | 4.9 | 10.0 |
| 19 | 4.2 | 11.2 |
| 20 | 5.2 | 10.2 |
| Average | 4.2 | 8.7 |
| STDEV | 1.4 | 2.6 |
| Accuracy (%) | 75.0% | |

**Note:
Subject 16 was classified as failure due to inability of the device to detect the membrane.

This test shows that the device can detect the difference in tissue pressures using a relatively constant applied force. It is believed that the device detects the membrane at edges because that is the transition zone during which the tissue difference is greatest. This causes the spring to push back against the tissue, disengaging the pin momentarily from the piezo element and engaging it back causing the LED to light.

Of the total 20 subjects tested, 4 were undetectable with the device. Subject 16 was a petite woman (<5 feet 2 inches) with a reduced CTM (~6.0 mm) length. Even with the ultrasound, operators had difficulty identifying the CTM. Of the three remaining, one was an obese elderly man (subject 13) with loose skin. Subject 14 and 15 had shortened necks. All these factors made it difficult to properly operate the device and gave false positives for detection. This gave the device an accuracy of 80.0% in correctly identifying the CTM.

Testing Constraints and Limitations
  Time: <1.0 minutes
  Variability: The variability in soft tissue among subjects. Thyroid cartilage angle and soft tissue height cannot be measured.
  Practitioners: Intermediate or basic paramedics are not readily available and only untrained subjects detected the CTM.
  Testing performed under a control environment where noise and stress are minimal.
  Limited sample size
  Limited amount of time
Conclusion
  With an accuracy result for combined and male population of 80% and 75% in female population, this experiment was successful in proving the device functionality. Considering the major demographic the device will be used on (males/females 18-60), this experiment showed much promise for the device.

3. Finite Element Analysis

Figure 17:
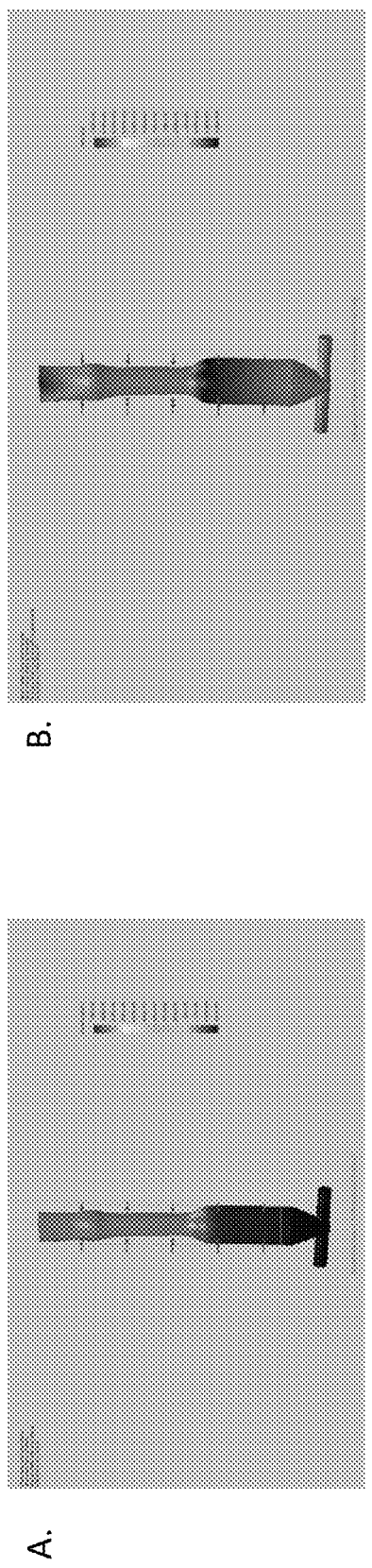
FIG. 17. Computer model of stress on a container of an embodiment of the invention subject to a 40 kPa blast pressure. Panel A shows peak von Mises stress under an applied concussive pressure of 40 kPa. Panel B shows URES static displacement plot under applied pressure of 40 kPa.
Figure 18:
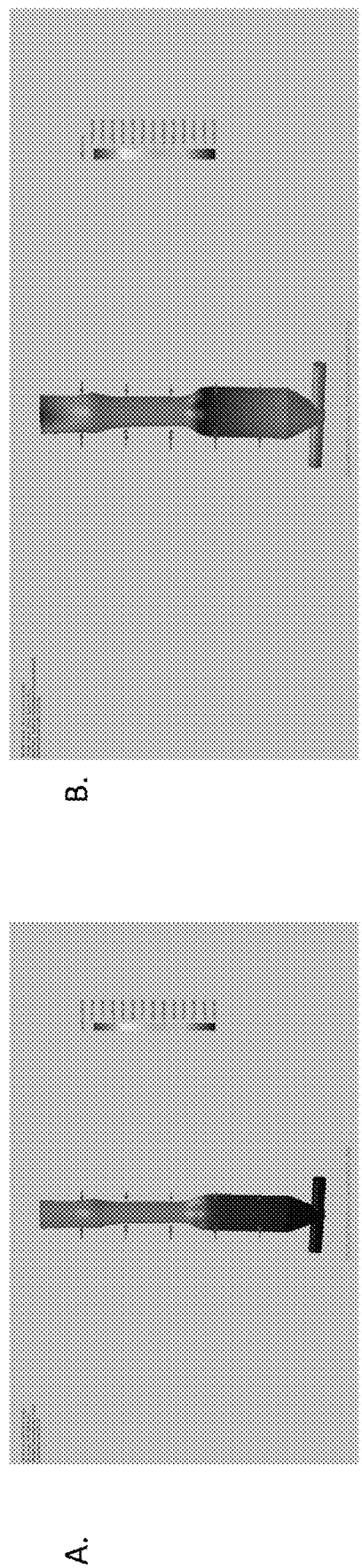
FIG. 18. Computer model of stress on a container of an embodiment of the invention subject to a 70 kPa blast pressure. Panel A shows peak von Mises stress under an applied primary shockwave of 70 kPa. Panel B shows URES static displacement plot under applied pressure of 70 kPa.
Figure 19:
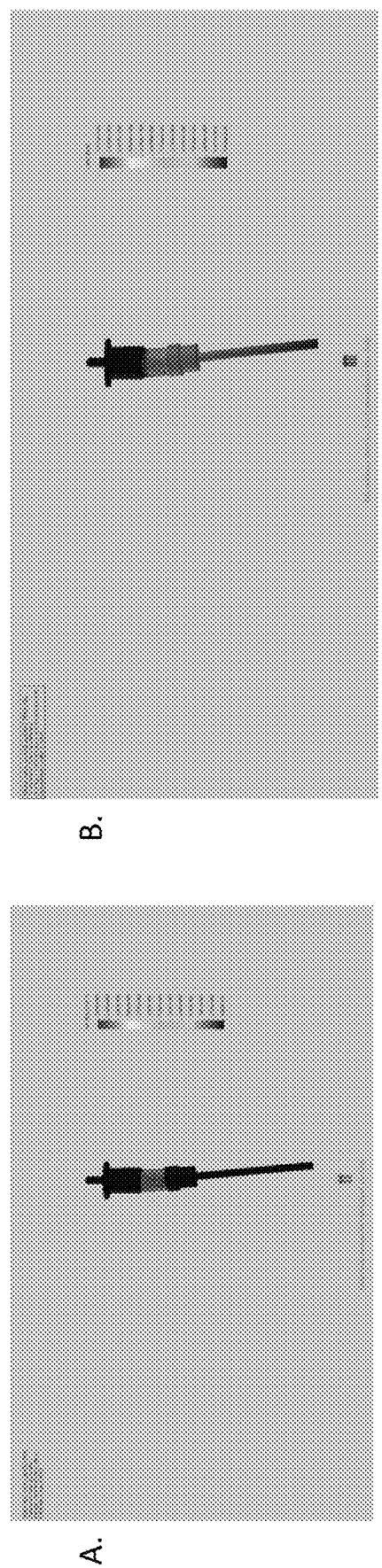
FIG. 19. Computer model of stress on a portion of an embodiment of the invention subject to a 2.0 N force. Panel A shows peak von Mises stress under an applied force of 2.0 N. Panel B shows URES static displacement plot under an applied force of 2.0 N.

Introduction:
  Computer simulation is arguably one of the best methods for making predictions about the performance of a specific structure prior to bench testing procedures. In this test, a finite element analysis model using computer software was used in order to examine the effects of an Improvised Explosive Device (IED) blast pressure wave applied directly to the device. Since the device is going to be used in emergency and battlefield conditions, knowing the deformation effects caused by the blast (the most common injury in the battlefield) on the device will help to determine if the material used, ultra-high molecular weight polyethylene (UHMWPE), is suitable to withstand these forces. Evaluation of Von Mises stresses is performed as well as examination of material's Young's Modulus to determine if material reaches failure.
Materials:
  SolidWorks software
Characteristics/Procedure:
  Testing Conditions
  Computer simulation modeling
  Study—"Static Motion"
  Material properties—UHMWPE
  Device position—vertically upward (LED on top)
  Fixed geometry—Top of device
  Applied force—2.0 N, pushing rod upward
  Shield
  Applied pressure—Primary and concussive shock wave, 70 and 40 kPa, respectively.
  Data Recording
  Images that show FEA simulations of stress, displacement (deformation) and strain. Legend explains color labeling.
Testing Constraints
  Computational power
  Limited by model geometry
  Complexity of the different shapes involved in the assembly
  Limited by mesh size
  Finer mesh—more computing time
  Coarser mesh—less computing time
Test Evaluation
  Test Criteria
    Definition of correct parameters established in testing conditions
  Test Tolerance
    Withstand the average force of 70 and 40 kPa from primary and concussive shock waves mimicking IED explosions.
  Plot
    N/A
  Data Reduction
    Manual collection
Results/Discussion
  It is anticipated that the device will be used in battlefield situations where a high probability of the device being exposed to explosive shock waves exists. Since it is crucial for the device to survive and function after such scenarios to serve battlefield medics in responding to traumatic injuries, the device was tested using Finite Element Analysis to ensure protective casing integrity under boundary conditions mimicking pressures representative of primary (70 kPa) and concussive (40 kPa) shock waves. Results shown in FIG. 17, Panel A confirm that the casing undergoes minimal deformation and that the peak Von Mises stress value of $3.09 \times 10^5$ Pa is well lower than the material strength of 0.69 GPa. For FIG. 17, Panel B shows URES static displacement plot under 40 kPa on the shield with a peak deformation of $7.135 \times 10{-3}$ mm FIG. 18, Panel A confirms that the shield undergoes minimal deformation and that the peak Von Mises stress value of $7.78 \times 10^5$ Pa is well lower than the material strength of 0.69 Pa. FIG. 18, Panel B shows URES static displacement plot under 70 kPa.
  Additionally, an analysis of the internal components during use, when a standard user applied force of 2.0 N is expected, showed a peak Von Mises stress of $9.343 \times 10^{-1}$ Pa which is lower than the endurance limit of our material 0.69 GPa and ensures an anticipated lifetime well in excess of a million cycles under non-extreme loading conditions. See FIG. 19, Panel A. Lastly, the components were analyzed using a URES static displacement plot under 2.0 N and the peak displacement was 6.57 mm See FIG. 19, Panel B. These tests show that the device can survive under extreme conditions and perform with significant durability under regular use.
  The shield and the internal compartments were analyzed separately because the design itself has a space between the internal compartments and the exterior, leading to not proper distribution of forces during simulation. The operator fixated the structures to have proper forces application.
  Testing Constraints
  Computational power
  Limited by model geometry
  Complexity of the different shapes involved in the assembly
  Limited by mesh size
  Finer mesh—more computing time
  Coarser mesh—less computing time
Conclusion
  Finite Element Analysis is an excellent tool to predict the behavior of solid structures such as in the case of the cricothyroid membrane detector to predict potential design failure or fractures. In this test, the device was simulated under primary and concussive shockwaves of 70 and 40 kPa, respectively. The results showed neither the shield nor the internal components will suffer from fracture or extreme deformation under these pressures. This give confidence that the device can withstand one million cycles under standard operation condition and the shield will be able to protect the internal components under extreme conditions such as those experienced in the battlefield.

4. Time of Detection

Introduction:

The first part of testing was recording age, gender, cricothyroid membrane length, BMI (height and weight) for each subject. For simplicity of the test, BMI wasn't considered within the factors that affected the sensitivity of the device. Each subject was laid on a horizontal bench for the detection of the CTM in hyperextended position using the detection device. The time need to identify the CTM was recorded on an excel spread sheet and compared to time used with the ultrasound. A fast time of detection improves the survival rates of the procedure and decreases post-procedure complications.

Materials:
Sonosite M-turbo (SonoSite Inc., Bothell, Wash.)
Caliper/Ruler
Stop Watch
Characteristics/Procedure:
Testing Conditions
Sensing load on the device: 0-2.0 N (increments of 0.2 N)
Temperature: 21° C.
Atmospheric pressure: 1.0 atm
Humidity: N/A
Air flow: Laminar <2100 (Reynolds number)
Variables:
Testing subjects: Female and Male 18-45 yrs. (N=10)
Supine and Hyperextended neck position
Practitioners: Medical uncertified and untrained personnel with only device training (N=4)
Sensing area is in the midline of the neck going from the sternal notch to the thyroid cartilage
Detection Time: <30 sec
Force supply: Operators hand
Means of detection: Palpation and portable ultrasound
Data Recording
Detection times were manually collected and inputted into an excel spreadsheet when the LED lights up on the cricothyroid membrane. Portability was assessed depending on the user's ability to operate the device using a single hand during detection.
Test Evaluation
Test Criteria
Correct identification of CTM within +/−5.0 mm of longitudinal CTM midline (prototype matches ultrasound diagnosis)
Within 25 Sec considered a pass
PASS/FAIL portability (subjective).
1-10, 1 being easiest and 10 being hardest
Test Tolerance
80.0 to 90.0% successful identification in female and male subjects
+/−5.0 mm of longitudinal CTM membrane
+/−10 sec within median 15 sec detection time
0.0 to 2.0 N loading force
Data Reduction
Manual collection
Must identify the CTM<25 sec
The ultrasound detection matches the prototype with a 90% successful identification
Pass/Fail for portability according to users.
Statistical Analysis
Average and standard deviation (SD) for detection times in combined (N=20), male (N=15) and female population (N=5).

Results/Discussion

TABLE 5

Combine detection times for the device compared to ultrasound
Combined Population (N = 20)

| Subject | Device Time (Sec.) | Ultrasound Time (Sec.) |
| --- | --- | --- |
| 1 | 15 | 30 |
| 2 | 12 | 32 |
| 3 | 15 | 25 |
| 4 | 10 | 21 |
| 5 | 21 | 27 |
| 6 | 14 | 29 |
| 7 | 11 | 29 |
| 8 | 14 | 32 |
| 9 | 13 | 31 |
| 10 | 19 | 24 |
| 11 | 14 | 28 |
| 12 | 13 | 28 |
| 17 | 35 | 21 |
| 18 | 33 | 28 |
| 19 | 36 | 31 |
| 20 | 39 | 38 |
| Average | 19.625 | 28.375 |
| STDEV | 10.04 | 4.3030 |

**Note:
Subjects 13-19 were classified as failures due to the inability to detect the CTM with the device.

The detection times for successful detections are listed in the table above for comparison with an ultrasound. Table 5 shows that the device does have a faster detection time than the portable ultrasound for identification of the CTM. The average for device detection time is even faster than that for palpation (24 seconds)(Campbell et al. "The Accuracy of Detecting of Locating the Cricothyroid Membrane by Palpation—an intergender study" BMC ANESTHESIOLOGY 14.1 (2014): 108-. The table does however show that the device also has a much higher standard deviation. This means that the device is also less consistent than an ultrasound; it is important to note that even with one standard deviation above the mean, it is still barely greater than the ultrasound average. The standard deviations were decreased by separating out the subjects by gender (Tables 6 & 7).

TABLE 6

Male detection times for the device compared to the ultrasound
Men (18-43 year)

| Subject | Device Time (Sec.) | Ultrasound Time (Sec.) |
| --- | --- | --- |
| 1 | 15 | 30 |
| 2 | 12 | 32 |
| 3 | 15 | 25 |
| 4 | 10 | 21 |
| 5 | 21 | 27 |
| 6 | 14 | 29 |
| 7 | 11 | 29 |
| 8 | 14 | 32 |
| 9 | 13 | 31 |
| 10 | 19 | 24 |
| 11 | 14 | 28 |
| 12 | 13 | 28 |
| Average | 14.25 | 28 |
| STDEV | 3.11 | 3.33 |

**Note:
Subjects 13-15 were classified as failures due to the inability to detect the CTM with the device.

From Table 6, it can be seen that the device significantly decreased the time of detection in male patients. The device's time is a little over half the detection time of the ultrasound with an even lower standard deviation. These results coincide perfectly with the projected patients from the armed forces (Males 18-45), giving the device much promise. The 14.25-second average is almost 10 seconds lower than that found with palpation. Although the device appears to working better on men, the same cannot be said for the female patients. This may be because women have smaller cartilages and membrane and the device itself has a blunt rod tip. However, this can be improved by decreasing the probe diameter.

TABLE 7

Female detection times for the device compared to the ultrasound Women (18-30 year)

| Subject | Device Time (Sec.) | Ultrasound Time (Sec.) |
|---|---|---|
| 17 | 35 | 21 |
| 18 | 33 | 28 |
| 19 | 36 | 31 |
| 20 | 39 | 38 |
| Averege | 35.75 | 29.5 |
| STDEV | 2.5 | 7.047 |

** Note:
Subjects 16 were classified as failures due to the inability to detect the CTM with the device.

The less prominent thyroid cartilage in females made it much more difficult for the device to detect the CTM. The device detects the transition from one tissue to another, hence having a smaller cartilage can lead to decreasing the sensitivity. This issue can be addressed by using a probe with a smaller diameter. Increased sensitivity should improve detection times, but the current times are still sufficient. In some instances, the device would need to pass down the midline more than one time before it could detect the membrane. Multiple trials can dramatically increase the average detection time, putting it slightly over the ultrasound. The device did have a lower standard deviation but this is due to the very low sample size and the low outlier of 21 seconds for detection.

Testing Constraints
Time: <1.0 minutes
Variability: The variability in soft tissue among subjects. Thyroid cartilage angle and soft tissue height cannot be measured.
Practitioners: Intermediate or basic paramedics are not readily available and only untrained subjects detected the CTM.
Testing was performed under a control environment where noise and stress were minimized
Limited sample size
Limited amount of time
Conclusions The average time of detection was less than 30 seconds specified in the testing criteria, meaning the test was a success. The device had a lower average time of detection than that found for palpation and ultrasound. When only considering women, the device performed slower than ultrasound. Increasing the sensitivity of the device should improve detection times in women. Mechanical means for detection offered the fastest and simplest means of detection of those tested.

5. Portability

Introduction:
Ambulances have limited space for supplies in emergency care situations; the space becomes even smaller for combat medics who carry all their supplies on them. Weight is also incredibly important when considering a combat medic must travel on foot, excessive weight can be dangerous in emergency situations. This makes it impractical to take diagnostic devices such as an ultrasound. For these reasons it is important to consider portability when testing the device. Portability, in this case, is defined by being able to handle the device with one hand and lightweight (<2 lbs.). For our portability test the device was weighed and measured and compared against average military personal measurements.

Materials:
Bench Top Balance
Caliper/Ruler
Characteristics/Procedure:
Testing Conditions
Temperature: 21° C.
Atmospheric pressure: 1.0 atm
Humidity: N/A
Air flow: Laminar <2100 (Reynolds number)
Data Recording
Measurements for the height, weight, and diameter were gathered and recorded.
Testing Constraints
Balance limit 0.001 g
Caliper limit 0.01 mm
Test Evaluation
Test Criteria
  Device circumference must be within the average length of one hand (cm) and weight under 2 lbs.
  Pass/Fail criteria
Data Reduction
  Automated collection
    Weight
    Height
  Manual collection
    Pass/Fail criteria
Excel spreadsheet
Test Procedure
1. Using the balance, the weight of the device was measured and recorded.
2. Using the caliper, the length and diameter of the device was measured and recorded.
3. The diameter was used to calculate the circumference which was compared to measurements of hands found in publications
Results/Discussion

TABLE 8

Summary of device dimensions
Dimensions

| Height | 14.7 cm |
|---|---|
| Diameter | 2.5 cm |
| Circumference | 7.85 cm |
| Weight | 89.4 g |
| | (0.197 lbs.) |

The device's weight was significantly lower that the surveyed devices weight for portability. With two pounds being the max weight, the device was about two tenth of that at 0.197 lbs. The average hand length for men and women, taken from "The Adult Human Hand: Some Anthropometric and Biomechanical Considerations" by Dr. Garrett, are 19.533 cm and 16.358 cm respectively. The device's circumference and length is well below both values. Lastly, the integrated circuit and sensor are already inside the device, therefore no extra accessories are necessary. These results show that the device is easily operated in one hand.

6. Conclusion

The device passed all the criteria for being portable. The size of the device allows it to be very practical in the field.

The portability of the device is a big advantage against ultrasound identification methods.

The proof of concept device with height, diameter and weight of 14.2, 2.5 cm and 89.4 grams, respectively, has an accuracy of 80% (N=20) with an average detection time in men of (N=15) 14.2+/−3.1 sec. The device detected an avg. force of 2.07+/−0.28 N and had an experimental spring constant of 290.97 N/m. The FEA confirmed the durability of our device under extreme conditions with a stress withstand of >70 kPa and 1 million cycles under standard conditions.

All patents and publications mentioned and/or cited in this specification are indicative of the level of those skilled in the art to which the invention pertains. All patents and publications mentioned and/or cited herein are incorporated by reference to the same extent as if each individual publication was specifically and individually indicated as having been incorporated by reference in its entirety.

What is claimed is:

1. A device for the mechanical detection of a specific underlying tissue in a subject, comprising a container, wherein the container comprises a probe, spring, sensor, and signal indicator, wherein when a mechanical force is applied to the probe, the force is transmitted to the sensor, whereby the sensor provides the signal indicator with a signal and the signal indicator provides an indication of detection of the specific underlying tissue in the subject,
wherein:
   i) the device is calibrated to detect thyroid cartilage and cricoid cartilage, the signal indicator does not provide an indication when pressed against the cricothyroid membrane and the signal indicator provides an indication when the device is pressed against one of the thyroid cartilage and the cricoid cartilage;
   ii) the device is calibrated to detect a cricothyroid membrane, the signal indicator provides an indication when the device is pressed against the cricothyroid membrane and the signal indicator does not provide an indication when pressed against one of the thyroid cartilage and the cricoid cartilage; or
   iii) the device provides a first momentary indicating signal when the device is pressed against one of thyroid cartilage and cricoid cartilage, and the device provides a second momentary indication when the device is transitioned by sliding and is pressed against a cricothyroid membrane.

2. The device of claim 1, wherein a first end of the probe contacts a spring within the container and a second end of the probe protrudes outside of the container.

3. The device of claim 1, wherein the container further comprises a spring pin and wherein a first end of the probe contacts the spring pin and a second end of the probe protrudes outside of the container.

4. The device of claim 1, wherein the spring is made of steel with a spring constant of about k=333.33 N/m.

5. The device of claim 4, wherein the spring consists of 8-14 coils, with a spring diameter of about 0.014 m and a wire thickness of about 0.001 m.

6. The device of claim 1, wherein the container comprises a horizontal member or a flange that protrudes from an end of the container perpendicular to a major axis of the container.

7. The device of claim 1, wherein the sensor is a piezoelectric force transducer.

8. The device of claim 7, wherein the sensor is capable of measuring a force of 2 N and is capable of sending an output of 2 Volts.

9. The device of claim 1, wherein the signal indicator is a light emitting diode (LED).

10. The device of claim 1, wherein the container has a cylindrical shape, wherein one end of the container is connected to the signal indicator and the probe protrudes from an opposing end of the container.

11. The device of claim 1, wherein the signal indicator is an LED that turns on when pressed against thyroid or cricoid cartilage but does not turn on when pressed against the cricothyroid membrane.

12. The device of claim 1, wherein the signal indicator is an LED that turns on when the probe is transitioned from pressing against thyroid or cricoid cartilage to pressing against cricothyroid membrane.

13. The device of claim 1, wherein the device detects a change in elasticity of underlying tissues.

14. The device of claim 13, wherein the signal indicator momentarily provides an indication when the probe is pressed against thyroid or cricoid cartilage and again momentarily provides an indication when the probe is transitioned to pressing against cricothyroid membrane.

15. The device of claim 14, wherein the indication is a light provided by an LED.

16. The device of claim 1, wherein the sensor is a balloon.

17. The device of claim 16, wherein the balloon has a volume of about $9.17 \times 10^{-7}$ m$^3$ and an internal gauge pressure of about 60,069 Pascals.

18. The device of claim 16, wherein the signal indicator is a pressure gage.

19. The device of claim 18, wherein the pressure gage provides an indication of pressure of between about 0 and about 100 kPa.

20. The device of claim 18, wherein the pressure gage provides an indication at a pressure of about 27 kPa.

21. A kit comprising the device of claim 1 and a base configured to be placed on a subject's neck with a slot in the base over thyroid cartilage, cricothyroid membrane and cricoid cartilage.

22. A method of performing a cricothyrotomy, comprising locating the cricothyroid membrane with the device of claim 1 and performing an incision on the located cricothyroid membrane.

* * * * *